United States Patent
Kiyama et al.

(10) Patent No.: US 10,428,300 B2
(45) Date of Patent: Oct. 1, 2019

(54) CELL CULTURING DEVICE

(71) Applicant: HITACHI, LTD., Tokyo (JP)

(72) Inventors: Masaharu Kiyama, Tokyo (JP); Guangbin Zhou, Tokyo (JP); Takayuki Nozaki, Tokyo (JP)

(73) Assignee: HITACHI, LTD., Tokyo (JP)

( * ) Notice: Subject to any disclaimer, the term of this patent is extended or adjusted under 35 U.S.C. 154(b) by 165 days.

(21) Appl. No.: 15/027,485

(22) PCT Filed: Oct. 15, 2013

(86) PCT No.: PCT/JP2013/077987
§ 371 (c)(1),
(2) Date: Apr. 6, 2016

(87) PCT Pub. No.: WO2015/056302
PCT Pub. Date: Apr. 23, 2015

(65) Prior Publication Data
US 2016/0244711 A1     Aug. 25, 2016

(51) Int. Cl.
*C12M 3/00*     (2006.01)
*C12M 1/00*     (2006.01)
*C12M 1/34*     (2006.01)

(52) U.S. Cl.
CPC ............ *C12M 41/34* (2013.01); *C12M 29/26* (2013.01)

(58) Field of Classification Search
CPC ...... C12M 29/24; C12M 29/20; C12M 23/24; C12M 23/04; C12M 23/42
See application file for complete search history.

(56) References Cited

U.S. PATENT DOCUMENTS 4,581,044 A * 4/1986 Uno ..................... B01D 53/047
                                                            95/139
5,652,142 A * 7/1997 Barker ................... C12M 25/04
                                                            422/536

(Continued)

FOREIGN PATENT DOCUMENTS

DE     102004005672 A1     8/2004
DE        69736124 T2      1/2007

(Continued)

OTHER PUBLICATIONS

English translation of Osuge et al, JP 2004-041093 (Year: 2004).*

(Continued)

*Primary Examiner* — Nathan A Bowers
(74) *Attorney, Agent, or Firm* — Baker Botts L.L.P.

(57) ABSTRACT

Maintaining pressure inside a culturing vessel is difficult when minimizing the size of a liquid supply path that supplies liquid and gas to a cell culturing vessel that performs two-level culturing (co-culturing). This cell culturing device includes: culturing vessels; a flow path having at least first supply ports capable of supplying liquid or gas to the culturing vessels and first discharge ports that discharge the gas from the culturing vessels, said flow path discharging gas from the first discharge ports to the atmosphere; and a filter in the flow path. A trap bottle is provided between the first discharge ports and the filter upon the flow path to collect moisture from the discharged gas. Thus, a liquid phase and a gas phase are separated in the trap bottle; moisture is prevented from reaching the filter; filter clogging is prevented; and the internal pressure of the culturing vessels can be maintained.

14 Claims, 9 Drawing Sheets

(56) References Cited

U.S. PATENT DOCUMENTS

| | | | |
|---|---|---|---|
| 5,820,641 | A | 10/1998 | Gu et al. |
| 2010/0105125 | A1 | 4/2010 | Haley, III |
| 2010/0279395 | A1 | 11/2010 | Haley, III |
| 2012/0260671 | A1 | 10/2012 | Damren et al. |
| 2013/0115690 | A1* | 5/2013 | Nakajima ............... C12M 23/10 435/297.1 |
| 2013/0143307 | A1 | 6/2013 | Nozaki et al. |
| 2014/0329224 | A1* | 11/2014 | Arnold ................... C12M 23/28 435/3 |
| 2014/0342447 | A1* | 11/2014 | Aviles ...................... C12Q 1/22 435/297.1 |
| 2015/0072401 | A1 | 3/2015 | Nozaki et al. |

FOREIGN PATENT DOCUMENTS

| | | |
|---|---|---|
| EP | 1498475 A1 | 1/2005 |
| EP | 1978089 A1 | 10/2008 |
| EP | 2604680 A1 | 6/2013 |
| JP | 2004-041093 A | 2/2004 |
| JP | 2004-329145 A | 11/2004 |
| JP | 2007-222120 A | 9/2007 |
| JP | 2007-312668 A | 12/2007 |
| JP | 2011-010599 A | 1/2011 |
| JP | 2012-506700 A | 3/2012 |
| JP | 2013-506424 A | 2/2013 |
| WO | WO 2011/001995 A1 | 1/2011 |
| WO | WO-2012008368 A1 * | 1/2012 ............ C12M 23/10 |
| WO | WO 2012/020458 A1 | 2/2012 |
| WO | WO 2013/053779 A1 | 4/2013 |
| WO | WO 2013/145235 A1 | 10/2013 |

OTHER PUBLICATIONS

Extended European Search Report, dated May 9, 2017, which issued during the prosecution of European Patent Application No. 13895619.8, which corresponds to the present application.

International Search Report, dated Jan. 14, 2014, which issued during the prosecution of International Patent Application No. PCT/JP2013/077987, which corresponds to the present application.

* cited by examiner

CELL CULTURING DEVICE

CROSS REFERENCE TO PRIOR APPLICATIONS

This application is a U.S. National Phase application under 35 U.S.C. § 371 of International Application No. PCT/JP2013/077987, filed on Oct. 15, 2013. The International application was published in Japanese on Apr. 23, 2015 as WO 2015/056302 A1 under PCT Article 21(2). The contents of the above applications are hereby incorporated by reference.

TECHNICAL FIELD

The present invention relates to an automatic cell culture system that cultures cells and a liquid sending device.

BACKGROUND ART

In regenerative medicine in which diseases are treated using the cells of a patient or the cells of a person other than the patient, cells extracted from a living body are often cultured to increase the number of cells, or tissue is grown in a certain form, and then used for transplantation treatment. Cells used for treatment have to be cultured in a clean room for cell culture, which is referred to as a cell processing center (CPC), in compliance with the good manufacturing practice (GMP). Problems here are in that cell culture is conducted by biologists and the preparation of cells for a patient takes a lot of effort, time, and costs, and in that risks of biological contamination arise by manual manipulation.

For the schemes of solving the problems, a system that automates cell culture processes in a closed system is developed. The automatic system includes a closed culture vessel that needs no manipulation of opening and closing the lid of the culture vessel, a liquid sending system, and an air supply system. In the entire automatic system, cells are cultured in the sealed state in which bacterial cells and viruses are prevented from entering. Thus, the cell culture processes are automated, and the risks of biological contamination are reduced.

On the other hand, in cells, some cell species need a growth factor produced from vegetative cells, which are feeder cells, in the process of growing cells, whereas some cell species need no growth factor. Cell species, such as embryonic stem (ES) cells and induced pluripotent stem (iPS) cells, on which attention is focused in regenerative medicine, skin epidermal cells, corneal epithelial cells, and oral epithelial cells, usually need feeder cells. In the case in which cultured cells are used for treatment, cells used for feeder cells and for treatment are desirably cultured as the cells are isolated from each other, and desirably cultured in a cell culture vessel having two culture layers. For schemes for solving this problem, a culture system described in Patent Literature 1 is proposed. In this system, a cell culture vessel having two culture layers is used and a flow channel that supplies or discharges cells or a culture medium is provided. Thus, cell species, such as ES cells, can be automatically cultured in a closed system. A culture system described in Patent Literature 2 is proposed as a system that implements automatic culture of cell species with no need of feeder cells in the process of growing cells. Patent Literature 2 discloses an automatic culture system that cultures cells, which are mainly stem cells, in a single culture layer.

CITATION LIST

Patent Literature

Patent Literature 1: Japanese Unexamined Patent Application Publication No. 2011-10599
Patent Literature 2: Japanese Unexamined Patent Application Publication No. 2007-222120

SUMMARY OF INVENTION

Technical Problem

The cell culture vessel described in Patent Literature 1 includes a culture medium holding unit in a two-layer structure. A liquid sending tube and a waste tube are provided for each of the two layers for moving a liquid. The culture medium holding unit includes a gas permeable membrane and a substance permeable membrane. Thus, cells are cultured at a predetermined humidity and gas composition. On the other hand, in the automatic culture system described in Patent Literature 2, the culture vessel is hermetically kept. In the process of ventilation (gas exchange), a tube used for sending a liquid is used to supply a gas to the culture vessel.

In the concept of two-layer culture in a culture vessel with no gas permeable membrane on its outer surface, when a method is based on the method described in Patent Literature 2, a configuration is formed in which a first vessel and a second vessel each include a liquid sending tube and a discharge tube, and a tube exclusively used for ventilation and gas exchange is further provided. Since the gaseous phases in the inside of the culture vessels are connected to each other, one ventilation tube only has to be provided in common. It is easy for a manufacturer to prepare five tubes for configuring the culture vessel as described above.

However, in the case in which the liquid sending control unit is connected to the culture vessel in a longer distance, the provision of a fewer number of tubes is advantageous, because component costs can be curtailed. In addition, the purpose of automation is to allow parallel processing with a plurality of culture vessels. In order to implement the provision of a plurality of culture vessels, it is also important to reduce the number of tubes.

The present inventors further conducted investigation. As a result, the present inventors found a fact that when a liquid is sent to the first vessel, the liquid sending tube of the second vessel can be used as a ventilation tube, whereas when a liquid is sent to the second vessel, the liquid sending tube of the first vessel can be used as a ventilation tube. In other words, it is only required that the first and second vessels are each provided with a liquid sending tube and a discharge tube and thus four tubes are provided as the minimum number of tubes.

However, as described later, in the case in which this configuration is adopted, a liquid culture medium that has not reached the vessel remains in a liquid sending tube through which a liquid culture medium has been sent. After that, a gaseous phase is moved to send the remaining liquid culture medium to the discharge tube. The remaining liquid culture medium then reaches a disposed filter, which might clog the filter. In the case in which the filter is clogged, a problem arises in that the filter causes a resistance to pressure or a loss in pressure to change the internal pressure of the discharge tube or the culture vessel, leading to an unstable flow of a liquid or gas. A problem arises in that water vapor contained in a communicating gas reaches a filter, and clogs the filter, which causes a phenomenon similar to the above problem.

It is an object of the present invention to provide an automatic cell culture system that can solve the problems, can implement the provision of a plurality of culture vessels with no increase in the number of tubes, and can maintain the internal pressures of the culture vessels at a normal pressure.

Solution to Problem

In the present invention, in order to solve the problems, there is provided an automatic cell culture system including: a culture vessel; a first supply port that supplies a liquid or gas into the culture vessel; a first outlet port that discharges a gas inside the culture vessel; a flow channel for discharging the gas discharged from the first outlet port to outside air at an atmospheric pressure; a filter provided on the flow channel; and a collecting unit provided between the first outlet port and the filter on the flow channel, the collecting unit collecting moisture in the discharged gas.

Advantageous Effects of Invention

In accordance with the automatic cell culture system according to the present invention, the internal pressure of the culture vessel can be maintained at a normal pressure.

DESCRIPTION OF EMBODIMENTS

In the following, embodiments of the present invention will be described. Prior to describing the embodiments, problems will be described with reference to FIGS. 2 and 4. These problems were found in investigating an automatic cell culture system in order to provide a plurality of culture vessels with no increase in the number of tubes.

Figure 2:
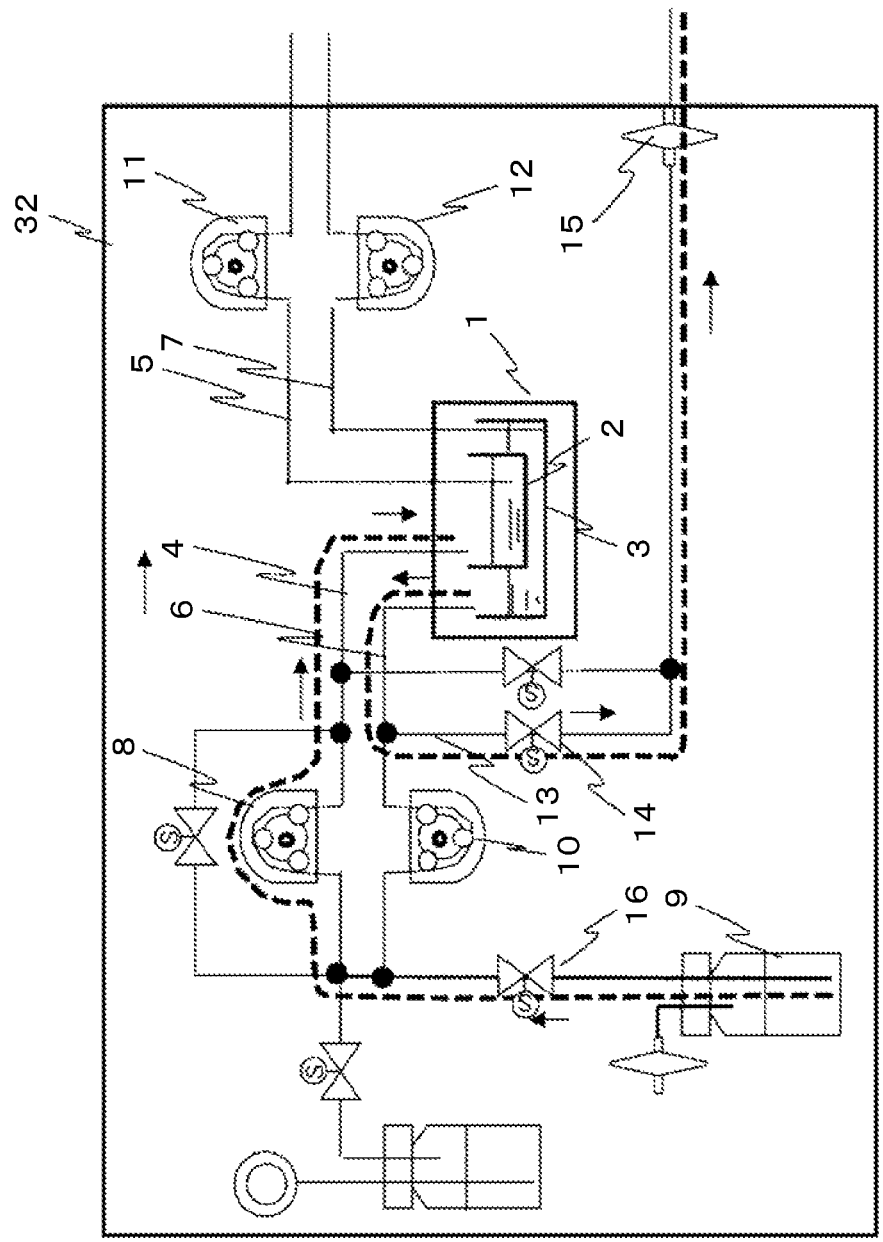
FIG. 2 is a diagram of the configuration of a liquid sending device of the automatic cell culture system in the state in which a liquid is sent.

FIG. 2 is a schematic diagram of a liquid sending and discharge unit for a culture vessel in an automatic cell culture system. Two-layer culture is conducted in the culture vessel. In FIG. 2, a culture vessel 1 is disposed in a thermostat 32. The culture vessel 1 is configured of a first vessel 2 and a second vessel 3, and allows two-layer culture. The first vessel 2 is provided with a liquid sending tube 4 that adds a liquid culture medium to the first vessel and a discharge tube 5 that discharges the liquid culture medium from the first vessel. The opening end on the vessel side is provided near the bottom face of the vessel. On the second vessel 3, a liquid sending tube 6 and a discharge tube 7 are also similarly provided. The liquid sending tube 4 that adds the liquid culture medium to the first vessel 2 is connected to a liquid bottle 9 that holds a liquid culture medium to be sent to the first vessel 2 through a first pump 8 and a liquid on-off valve 16. The liquid sending tube 6 that adds a liquid culture medium to the second vessel 3 is connected to the liquid bottle 9 that holds a liquid culture medium to be sent to the second vessel 3 through a second pump 10. Among these components, the liquid sending tube 6 is branched into two passages between the second pump 10 and the midway point to the culture vessel 1, and is opened as a discharge tube 13 to the atmosphere through a discharge on-off valve 14 and an air communication filter 15.

From the discharge tube 5 that discharges the liquid culture medium from the first vessel 2, the liquid culture medium is discharged to a recovery bottle, not illustrated, through a third pump 11. From the discharge tube 7 that discharges the liquid culture medium from the second vessel 3, the liquid culture medium is discharged to a recovery bottle, not illustrated, through a fourth pump 12.

In sending a liquid to the culture vessel that conducts two-layer culture, after the liquid on-off valve 16 and the discharge on-off valve 14 are opened to operate the first pump 8, a liquid starts to move along the orientation of broken lines and arrows from the liquid bottle 9, passes through the liquid sending tube 4, and then reaches the inside of the first vessel 2 of the culture vessel 1. When the third pump 11 and the fourth pump 12 for discharge are not operated, the culture vessel 1 is closed like a valve, and the discharge side is hermetically kept. At this time, the gaseous phase of the culture vessel passes and communicates through the liquid sending tube 6 along the orientation of broken lines and arrows. The gaseous phase communicates with the atmosphere through the opened discharge on-off valve 14. Thus, the pressure inside the vessel is maintained at an atmospheric pressure in the process of sending a liquid. In other words, the liquid sending tube of the second vessel, which is originally used for sending a liquid, can be used as a ventilation tube. Thus, tubing exclusively used for ventilation can be eliminated. Consequently, the number of tubes can be decreased.

Figure 3:
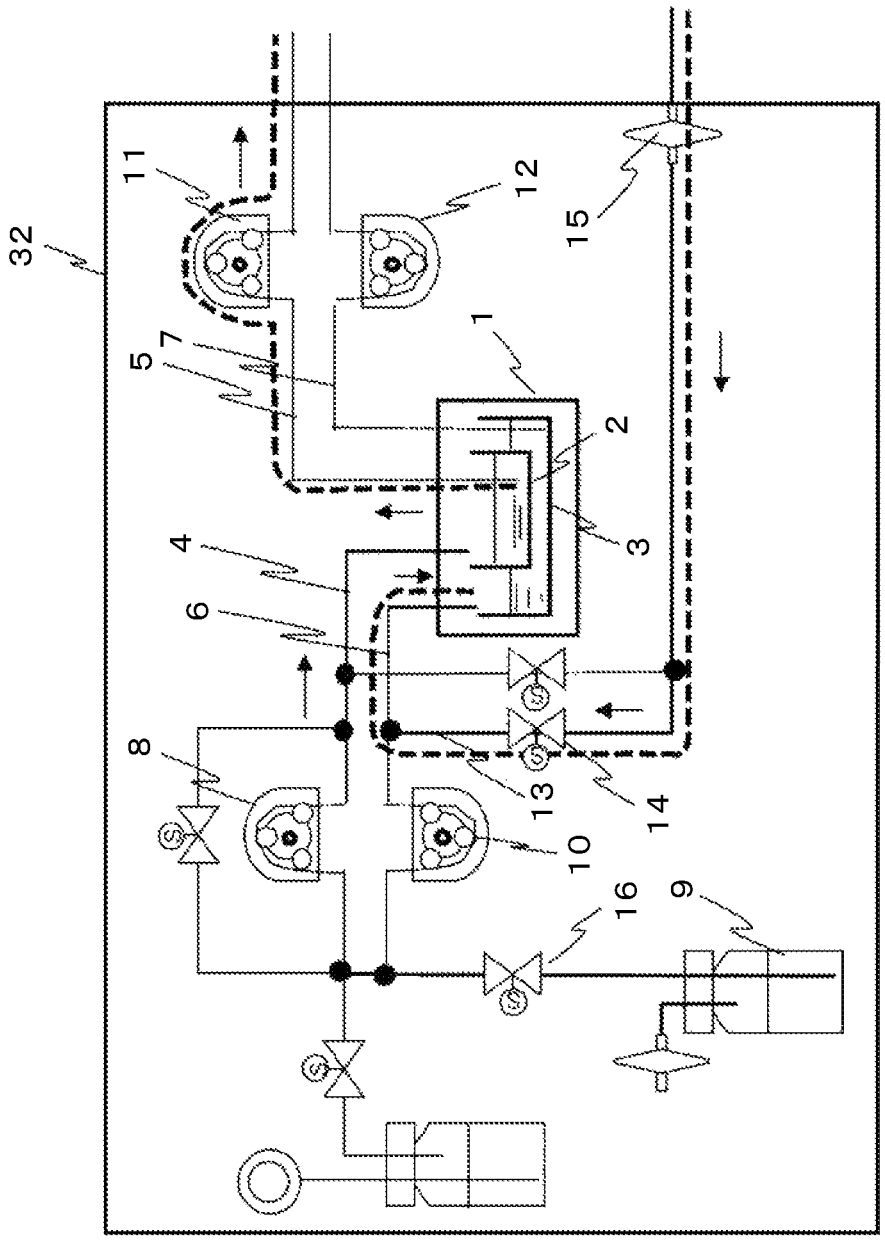
FIG. 3 is a diagram of the configuration of the liquid sending device of the automatic cell culture system in the state in which a liquid is discharged.

Next, FIG. 3 is a diagram of a discharge method for the culture vessel that conducts two-layer culture in the configuration in FIG. 2. In discharging a liquid, after the discharge on-off valve 14 is opened to operate the third pump 11, a liquid starts to move along the orientation of broken lines and arrows from the first vessel of the culture vessel 1, passes through the discharge tube 5, and then reaches the recovery bottle, not illustrated. When the first pump 8 for sending a liquid and the fourth pump 12 for discharging a liquid are not operated, the culture vessel 1 is closed like a valve, and kept hermetically. Thus, the gaseous phase inside the culture vessel communicates with the atmosphere, because the liquid sending tube 6 communicates with the atmosphere from the port opened to the atmosphere through the air communication filter 15 and the opened discharge on-off valve 14 along the orientation of broken lines and arrows. Consequently, the pressure inside the vessel is maintained at an atmospheric pressure in the process of sending a liquid. In other words, the liquid sending tube of the second vessel, which is originally used for sending a liquid, can be used as a ventilation tube. Thus, in discharging a liquid, tubing exclusively used for ventilation is eliminated.

Figure 4:
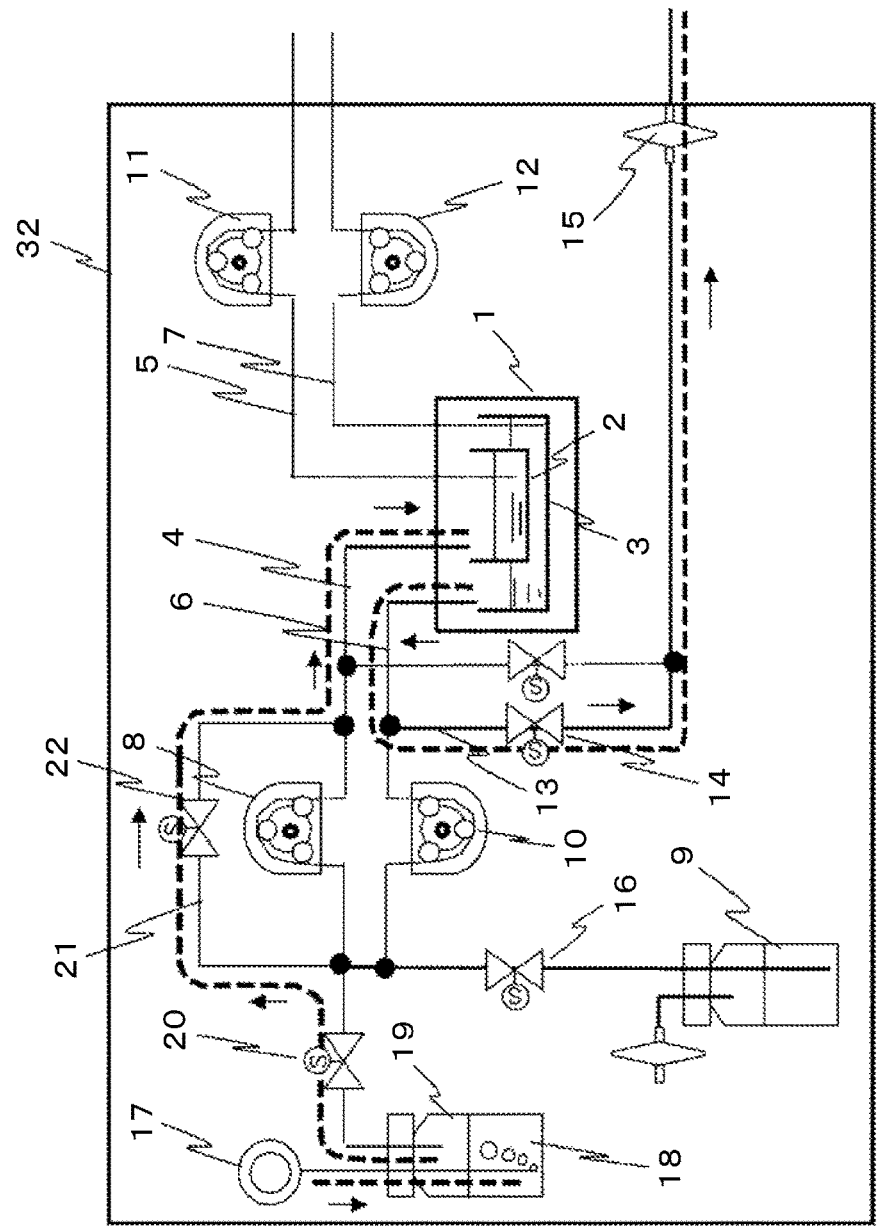
FIG. 4 is a diagram of the configuration of the liquid sending device of the automatic cell culture system in the state in which a gas is ventilated.

Next, FIG. 4 is a diagram of a ventilation method for the culture vessel that conducts two-layer culture in the configurations in FIGS. 2 and 3. A mixed gas cylinder 17 containing $CO_2$ and $O_2$ is connected to a sparger bottle 19. In order to prevent the pH value from being changed over time in the liquid culture medium in culturing cells, it is necessary to periodically exchange a gas from the surface of the liquid culture medium with the gases. In addition, it is necessary to prevent liquid culture medium components from being condensed due to the evaporation of the liquid culture medium. The $CO_2$ gas sent from the cylinder 17 is passed into pure water 18 in the sparger bottle 19, and the gas is humidified at the optimum humidity, and ready for use. The gas passes through a first gas on-off valve 20, a second gas on-off valve 22 provided on a gas tube 21 bypassing the first pump 8, and the liquid sending tube 4, and then reaches the culture vessel 1. Thus, the gases in the vessel can be exchanged, and humidity can be maintained.

In the ventilation of gases to the culture vessel that conducts two-layer culture, after the discharge on-off valve 14 is opened and then the second gas on-off valve 22 and the first gas on-off valve 20 are opened, the humidified gas starts to move from the sparger bottle 18 along the orientation of broken lines and arrows, passes through the gas tube 21 and the liquid sending tube 4, and then reaches the gaseous phase of the culture vessel 1. In the culture vessel 1, the liquid sending tube 6 communicates with the atmosphere through the opened discharge on-off valve 14 similarly as described above. Thus, the gaseous phase in the culture vessel 1 is replaced with the gas, and released to the atmosphere. The pressure inside the vessel is maintained at a controlled pressure in the process of sending a gas. In other words, the liquid sending tube 4 of the second vessel, which is originally used for sending a liquid, can be used as a ventilation tube, and the liquid sending tube 6 of the first vessel can be used as a ventilation discharge tube. Thus, in the ventilation of gases, tubing exclusively used for ventilation can be eliminated.

As briefly described above, in the configurations above, a liquid culture medium that has not reached the vessel remains in the liquid sending tube through which a liquid culture medium has been sent. After that, a gaseous phase is moved to send the liquid culture medium to the discharge tube. The liquid culture medium reaches the air communication filter, which might clog the filter. In the case in which the filter is clogged, the filter causes a resistance to pressure or a loss in pressure to change the internal pressure of the discharge tube or the culture vessel, leading to an unstable flow of a liquid or gas.

For one example, in the case in which the internal pressure of the culture vessel becomes higher than the atmospheric pressure, the discharge tube 5 and the discharge tube 7 are in contact with the liquid culture medium, and thus the liquid culture medium is entered to the discharge tube, and the liquid culture medium, which is originally held on the vessel 1 or vessel 2, is decreased. In the case in which the internal pressure becomes lower than the atmospheric pressure, the discharge tube 5 and the discharge tube 7 are in contact with the liquid culture medium, and thus the gaseous phase in the discharge tube becomes small bubbles, and the bubbles remain in the liquid culture medium. Originally, the liquid culture medium and cells held in the vessel 1 or vessel 2 desirably include no bubbles. After the liquid is continuously sent with the air communication filter being clogged, the liquid culture medium that has not reached the vessel starts accumulation in the discharge tube, and the tube itself is clogged to be a pressure resistance. This leads to a failure of maintenance of the reproducibility of sending a predetermined amount of a liquid to the culture vessel.

In some cases, water vapor contained in a communicating gas reaches the air communication filter to clog the filter. The resulting phenomenon is the same as the phenomenon described above.

The present invention can solve the problems described above. Embodiments of the present invention will be described in detail with reference to the accompanying drawings. However, these embodiments are merely examples to implement the present invention, which have no limitation on the technical scope of the present invention.

First Embodiment

Figure 5:
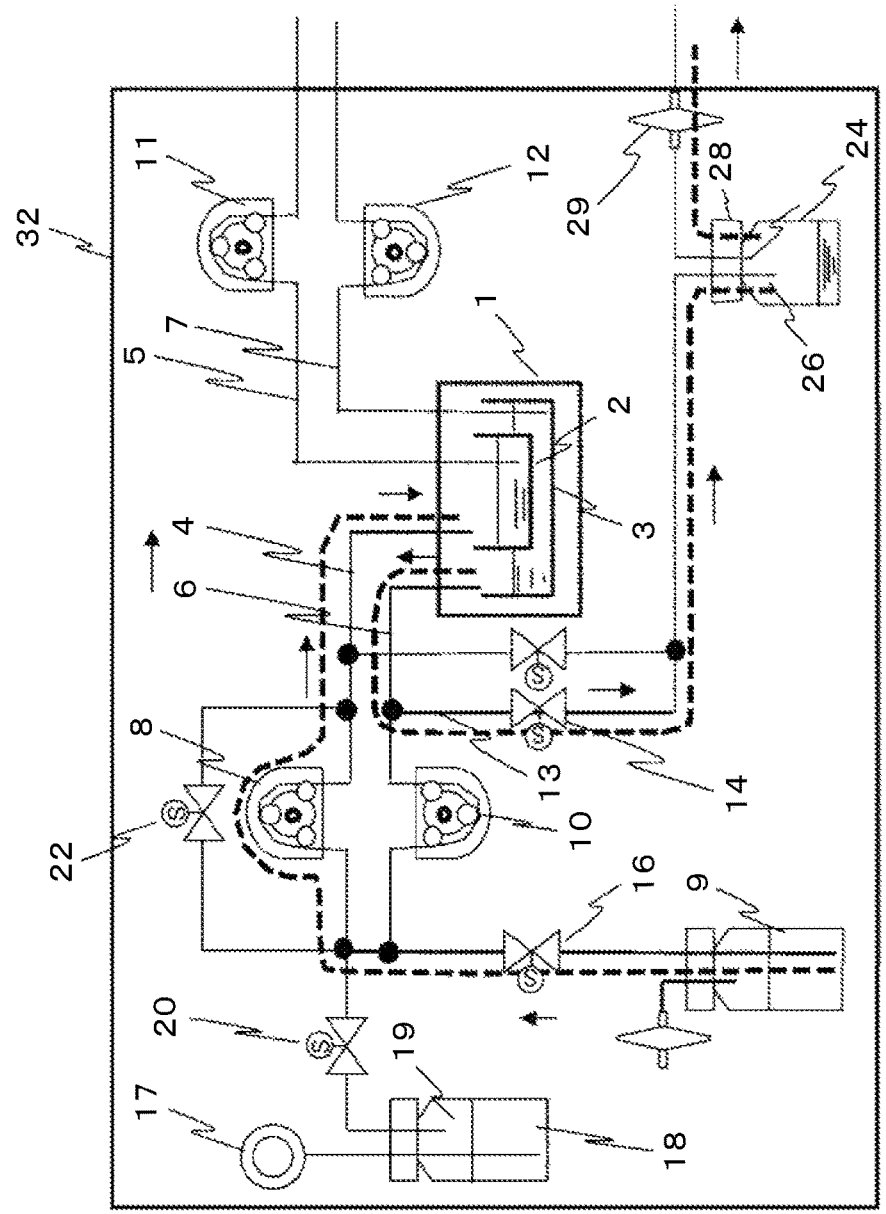
FIG. 5 is a diagram of the liquid sending device of the automatic cell culture system according to the first embodiment in the state in which a liquid is sent.

Referring to FIG. 5, a first embodiment of an automatic cell culture system will be described. FIG. 5 is a diagram of a configuration in which a trap bottle is disposed as a collecting unit that collects liquids, such as moisture, in the configuration in FIG. 2, which is a schematic diagram of the liquid sending and discharge unit of the culture vessel that conducts two-layer culture. The configurations of the components from the liquid sending unit to a culture vessel 1 are the same as the configurations described above. Thus, the description of the components from the culture vessel 1 to a discharge on-off valve 14 is omitted. A trap bottle 24 is hermetically kept with a lid 28. The lid is provided with a vessel side opening 26 and an atmosphere side opening 27 penetrated through the lid. The vessel side opening 26 is connected to a discharge tube 13 through the discharge on-off valve 14. The atmosphere side opening 27 is opened to the atmosphere through an air communication filter 29.

In sending a liquid to the culture vessel that conducts two-layer culture, after the discharge on-off valve 14 is opened to operate the first pump 8, a liquid starts to move from the liquid bottle along the orientation of broken lines and arrows, passes through the liquid sending tube 4, and then reaches the inside of the first vessel 2 of the culture vessel 1. When the third pump 11 and the fourth pump 12 for discharge are not operated, the culture vessel 1 is closed like a valve, and the discharge side is hermetically kept. At this time, the gaseous phase of the culture vessel passes and communicates through the liquid sending tube 6 along the orientation of broken lines and arrows, passes through the opened discharge on-off valve 14 and the trap bottle 24, and communicates with the atmosphere. Thus, the pressure inside the vessel is maintained at an atmospheric pressure in the process of sending a liquid.

Subsequently, a liquid culture medium that has not reached the vessel remains in the liquid sending tube through which a liquid culture medium has been sent. The gaseous phase then moves to send the remaining liquid culture medium, and the liquid culture medium reaches the trap bottle 24. The liquid having passed through the inside of the liquid sending tube and reached the trap bottle 24 is condensed at the vessel side opening 26, and then dropped onto the inner bottom part of the bottle. The gaseous phase passes through the atmosphere side opening 27 communicating inside the bottle, reaches the air communication filter 29, and then is released to the atmosphere.

Next, a ventilation method for the culture vessel that conducts two-layer culture 1 is described. A mixed gas cylinder 17 containing $CO_2$ and $O_2$ is connected to a sparger bottle 19. The $CO_2$ gas sent from the cylinder 17 is passed into pure water 18 in the sparger bottle 19, and the gas is humidified at the optimum humidity, and ready for use. The gas passes through a first gas on-off valve 20, a second gas on-off valve 22 provided on a gas tube 21 bypassing the first pump 8, and the liquid sending tube 4, and then reaches the culture vessel 1.

Figure 6:
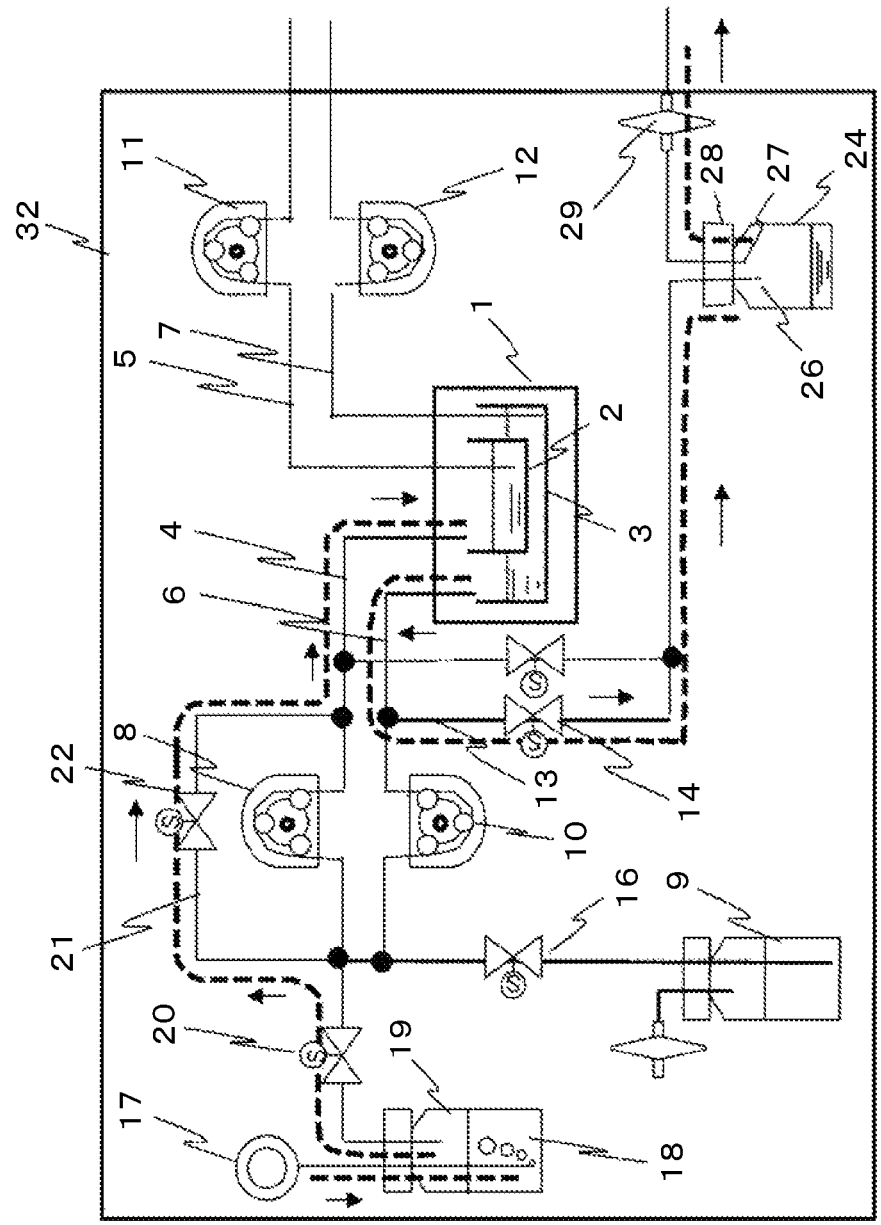
FIG. 6 is a diagram of the liquid sending device of the automatic cell culture system according to the first embodiment in the state in which a gas is ventilated.

As illustrated in FIG. 6, in the ventilation of gases to the culture vessel that conducts two-layer culture, after the discharge on-off valve 14 is opened and then the second gas on-off valve 22 and the first gas on-off valve 20 are opened, the humidified gas starts to move from the sparger bottle 18 along the orientation of broken lines and arrows, passes through the gas tube 21 and the liquid sending tube 4, and then reaches the gaseous phase of the culture vessel 1. At this time, the gaseous phase of the culture vessel passes and communicates through the liquid sending tube 6 along the orientation of broken lines and arrows, and communicates with the atmosphere through the opened discharge on-off valve 14. Thus, the pressure inside the vessel is maintained at an atmospheric pressure in the process of ventilation of a gas.

When water vapor contained in a communicating gas passes through the trap bottle 24 functioning as a collecting unit that collects moisture in a gas, the water vapor is separated into a liquid phase and a gaseous phase. Consequently, the liquid phase is prevented from reaching the air communication filter 29, and thus the filter can be prevented from being clogged.

In the configuration of the trap bottle 24, its material only has to be a material resistant to pressure and not deformed at an ambient temperature. The trap bottle 24 has to be sterilized before used for cell culture. Thus, materials, such as glass and a polycarbonate resin, are preferable. The sterilization of the trap bottle prior to use allows preventing untargeted bacteria and germs from growing even though the culture medium is held in the inside of the trap bottle, and the sterilized state of the flow channel connected to the trap bottle can be maintained. Ideally, the used trap bottle is removed together with the flow channel, and used one time. This can omit time and effort for cleaning and sterilization. A trap bottle made of a transparent material allows the confirmation of the stored state of a liquid inside the trap bottle, which is more preferable.

Desirably, the vessel side opening 26 and the atmosphere side opening 27 are penetrated through the lid. The height of the position of the opening end of the vessel side opening 26 is lower than the height of the position of the opening end of the atmosphere side opening 27. The liquid culture medium having moved, or the droplets of the condensed water vapor freely fall typically from the vessel side opening 26. Thus, the provision of the atmosphere side opening 27 below the vessel side opening 26 can prevent droplets from reaching the atmosphere side opening 27.

Valve mechanisms used for the liquid on-off valve 16 and other valves described above are preferably solenoid valves. A so-called solenoid valve is a mechanism in which a rubber tube is clamped, which means connected, to a component opened and closed by electromagnetic operation, and the solenoid valve is turned on and off to elastically deform the rubber tube for closing and opening the tube. In the following, the valves mean solenoid valves. Preferably, the pumps described above are typical roller pumps. A so-called roller pump is a mechanism in which a roller is mounted on a motor shaft, the roller is wound, which means connected, with a rubber tube, and a motor is rotated to elastically deform the rubber tube for sending a gas or a liquid inside the bottles. In the following, the pumps mean roller pumps. The filters described above are a filter that takes in a gas externally from the flow channel or discharges a gas for adjusting the atmospheric pressure in the inside of the flow channel. For example, filters having quality of blocking particles in particle size of 0.22 μm or greater, bacterial cells, and viruses are used. In the following, the filters mean similar ones.

<Configuration of the Automatic Cell Culture System>

Figure 1:
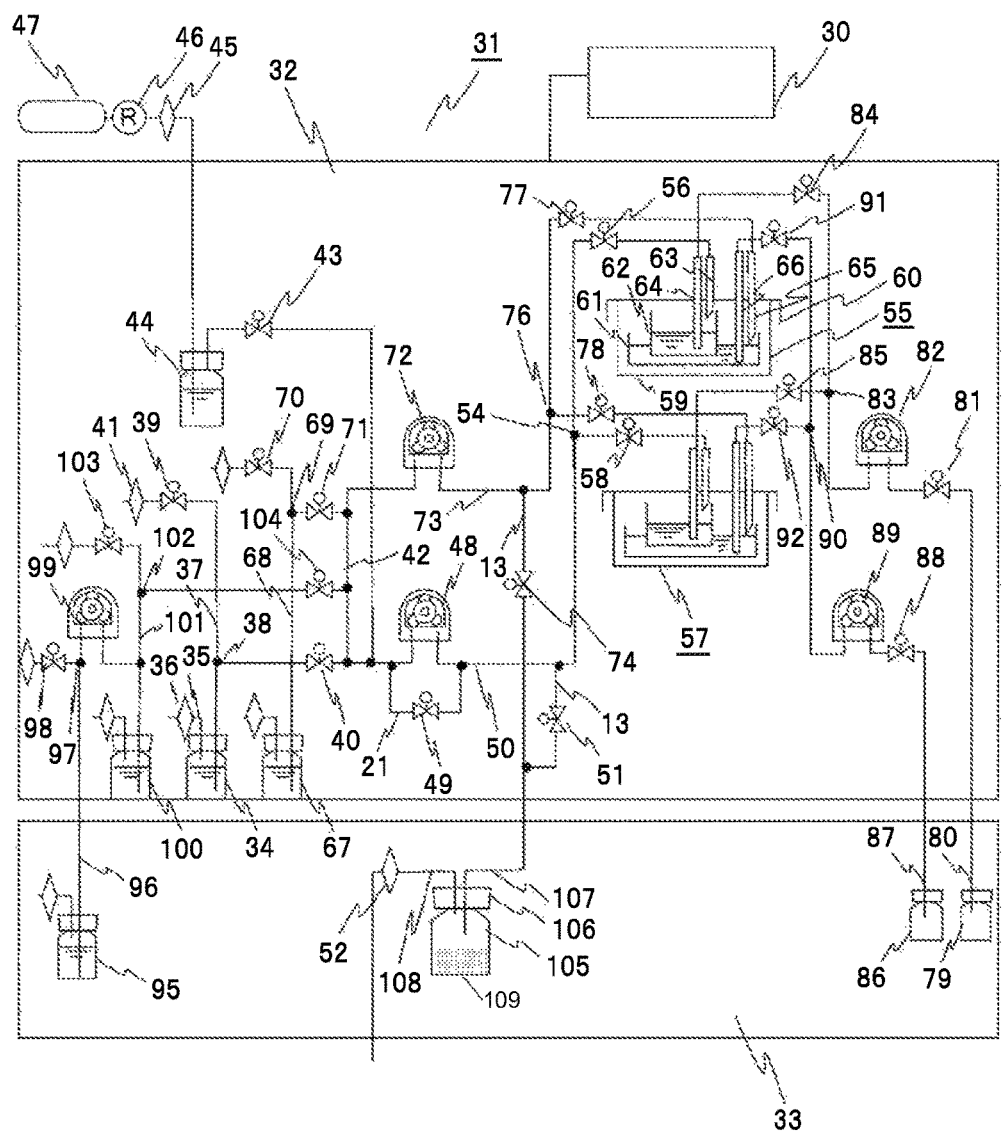
FIG. 1 is a diagram of an exemplary configuration of an automatic cell culture system according to a first embodiment.

FIG. 1 is a diagram of an exemplary configuration of the automatic culture system including the trap bottle as a collecting unit that collects a liquid, such as moisture, according to the first embodiment. In the following, the configuration and operation of an embodiment of an automatic cell culture system 31 including a liquid sending control unit that supplies or discharges a liquid culture medium to cell culture vessels will be described. A thermostat 32 holds cell culture vessels, described in detail below, at an optimum culture temperature for cell culture. A refrigerator 33 holds materials and components that have to be kept at low temperature. A controller 30 controls the mechanical components described above and mechanical components below along programmed sequences. In FIG. 1, culture vessels 55 and 57 correspond to the culture vessel 1 in FIGS. 5 and 6. A trap bottle 105 corresponds to the trap bottle 24. A first pump 48, a second pump 72, a third pump 82, and a fourth pump 89 correspond to the first pump 8, the second pump 10, the third pump 11, and the fourth pump 12, respectively.

A first cell bottle 34 that holds a first cell suspension is a liquid bottle that can hermetically hold the first cell suspension in its inside with a lid. The first cell bottle 34 includes a tube 35 provided on the lid for adjusting the atmospheric pressure. The first cell bottle 34 is opened to the inside of the thermostat 32 through a filter 36 provided at its opening end. One end of a supply tube 37 provided on the lid has the opening end in the inside of the first cell bottle 34. The one end is in contact with the cell suspension, and is a liquid outlet port. The supply tube 37 is branched into two passages through a branch point 38. One of the branches of the supply tube 37 is connected to a first gas inlet valve 39. The other of the branches of the supply tube 37 is connected to a first cell on-off valve 40. The branch point 38 is provided above the liquid level of a liquid held in the first cell bottle 34. A filter 41 is provided at the opening end of the supply tube 37, and opened to the inside of the thermostat 32.

The supply tube 37 branched at the branch point 38 is branched into two passages at the first cell on-off valve 40. One is connected to a common tube 42. The other is connected to a two-branch point to a first gas on-off valve 43. The common tube 42 will be described later. A sparger bottle 44 is connected to the first gas on-off valve 43. A filter 45 is connected to the sparger bottle 44. A mixed gas cylinder 47 containing $CO_2$ and $O_2$ is connected to the sparger bottle 44 through a pressure control valve 46. In order to prevent the pH value from being changed over time in the liquid culture medium in culturing cells, it is necessary to periodically exchange a gas from the surface of the liquid culture medium with $CO_2$ gas. In addition, it is necessary to prevent liquid culture medium components from being condensed due to the evaporation of the liquid culture medium. The $CO_2$ gas sent from the cylinder 47 is humidified at the optimum humidity in the sparger bottle, and ready for use.

The other of two branches of the supply tube 37 connected to the first gas on-off valve 43 is branched into two passages, the suction port of the first pump 48 and a second gas on-off valve 49. The discharge port of the first pump 48 and the second gas on-off valve 49 are combined to be a liquid sending tube 50. In other words, the second gas on-off valve 49 functions as a bypass for the first pump 48. Here, a tube for sending a liquid from the suction port of the pump to the cell bottle is a supply tube. A tube for sending a liquid from the discharge port of the pump to the culture vessel for cell culture is a liquid sending tube.

To one end of two branches of the liquid sending tube 50, the trap bottle 105, which is a collecting unit, is connected through the discharge tube 13 and a first discharge on-off valve 51. The trap bottle 105 is hermetically kept with the lid 106. A vessel side opening 107 and an atmosphere side opening 108 are penetrated through the lid 106. The trap bottle 105 itself is held in the inside of the refrigerator 33. The atmosphere side opening 108 is opened to the atmosphere through an air communication filter 52.

The liquid sending tube 50 is branched at a multi-branch part 54. One is connected to a first vessel on-off valve 56 for the first culture vessel 55. The other is connected to the first vessel on-off valve 58 for the second culture vessel 57. The first culture vessel 55 and the second culture vessel 57 have the same configuration, and correspond to the culture vessel 1 in FIGS. 5 and 6. Thus, in the following, the culture vessels will be described using the first culture vessel 55. In the automatic cell culture system according to the embodiment, the number of the culture vessels arranged side by side is not limited to two. Of course, three or more culture vessels can be arranged.

In the appearance, the first culture vessel 55 is a hermetical vessel including a main body 59 and a lid 60. In the inside, the first culture vessel 55 can hold a second vessel 61 and a first vessel 62 on the inner bottom part of the main body 59. The second vessel 61 can hold and culture cells. The first vessel 62 can hold and culture cells. In the first culture vessel 55, the culture surface of the first vessel 62 is formed of a substance permeable membrane. The first culture vessel 55 is a culture vessel that conducts a so-called co-culture, which is a culture method in which the membrane transmits only growth factors produced from vegetative cells cultured in the second vessel 61 for promoting the growth of cells cultured in the first vessel. The lid 60 has four penetrating ports, i.e., a first port 63 that adds a liquid to the first vessel 62, a second port 64 in contact with the region near to the bottom face of the first vessel 62 for discharging a liquid, a third port 65 that adds a liquid to the second vessel 61, and a fourth port 66 in contact with the region near to the bottom face of the second vessel 61 for discharging a liquid. As described in detail later, in the embodiment, the first port 63 and the third port 65 function as first supply ports to supply a liquid or gas to the first vessel 62 and the second vessel 61, respectively. The first port 63 and the third port 65 also function as first outlet ports to discharge a gas in the culture vessel 55.

The liquid sending tube 50 is connected to the first port 63 through the first vessel on-off valve 56. The cell suspension in the first cell bottle 34 is sent to the first vessel 62 of the first culture vessel 55 or the second culture vessel 57 by the operation of the first pump 48.

A second cell bottle 67 is a liquid bottle that holds a second cell suspension. A lid, a tube for adjusting the atmospheric pressure, a filter, and a supply tube 68 are the same as those of the first cell bottle 34, and the description is omitted. Similarly, the configuration of connecting the supply tube 68, a branch point 69, a second gas inlet valve 70, a filter, and a second cell on-off valve 71 is the same.

The supply tube 68 is branched into two passages through the second cell on-off valve 71. One is connected to the common tube 42. The other is connected to the suction port of the second pump 72. A liquid sending tube 73 extended from the discharge port of the second pump 72 is branched into two passages. To one of two branches, the trap bottle 105 is connected through the discharge tube 13 and a second discharge on-off valve 74.

Subsequently, the liquid sending tube 73 is branched at a multi-branch part 76, and connected to a second vessel on-off valve 77 for the first culture vessel 55 and to a second vessel on-off valve 78 for the second culture vessel 57. The second vessel on-off valve 77 is connected to the third port 65 that adds a liquid to the second vessel 61. In other words, in the tubing configuration, the cell suspension in the second cell bottle 67 is sent to the second vessel 61 of the first culture vessel 55 or the second culture vessel 57 by the operation of the second pump 72.

A culture medium bottle 95 according to the embodiment functions as a liquid bottle that holds a liquid culture medium for replacement. The culture medium bottle 95 is held in the refrigerator 33. The configurations of a lid, a tube for adjusting the atmospheric pressure, a filter, and a supply tube 96 are similar to the configurations of the first cell bottle 34. Similarly, the configuration of connecting the supply tube 96, a branch point 97, a third gas inlet valve 98, and a filter is the same. The suction port of a fifth pump 99 is connected to the supply tube 96. A culture medium preheater bottle 100 is a liquid bottle that holds a liquid culture medium for replacement only in a required amount. The culture medium preheater bottle 100 is connected to the discharge port of the fifth pump 99 through a supply tube 101 via a branched point. The culture medium preheater bottle 100 is held in the inside of the thermostat 32. In other words, in the tubing configuration, the liquid culture medium in the culture medium bottle 95 is sent to the culture medium preheater bottle 100 by the operation of the fifth pump 99.

The lid, the tube for adjusting the atmospheric pressure, the filter, and the supply tube 101 of the culture medium preheater bottle 100 are the same as those of the first cell bottle 34, and the description is omitted. Similarly, the configuration of connecting the supply tube 101, a branch point 102, a fourth gas inlet valve 103, a filter, and a culture medium on-off valve 104 is the same. The supply tube 101 is connected to the common tube 42 through the culture medium on-off valve 104 and then branched. One of the branches is connected to the supply tube 37 extended from the first cell bottle 34 through the first cell on-off valve 40. The other is connected to the supply tube 68 extended from the second cell bottle 67 through the second cell on-off valve 71.

In other words, the common tube 42 is connected to three on-off valves, i.e., the first cell on-off valve 40, the second cell on-off valve 71, and the culture medium on-off valve 104. In the tubing configuration, in operating the first pump 48, only the first cell on-off valve 40 is opened to send the liquid in the first cell bottle 34 to the first vessel 62 of the first culture vessel 55 or the second culture vessel 57. In operating the second pump, only the second cell on-off valve 71 is opened to send the liquid in the second cell bottle 67 to the second vessel 61 of the first culture vessel 55 or the second culture vessel 57. In operating the first pump 48, only the culture medium on-off valve 104 is opened to send the liquid culture medium held in the culture medium preheater bottle 100 to the first vessel 62 of the first culture vessel 55 or the second culture vessel 57. In operating the second pump, only the culture medium on-off valve 104 is opened to send the liquid culture medium held in the culture medium preheater bottle 100 to the second vessel 61 of the first culture vessel 55 or the second culture vessel 57.

Next, the configuration will be described in which the liquid held in the first culture vessel 55 or the second culture vessel 57 is discharged. A waste tube 80 is hermetically connected to a first waste bottle 79. The waste tube 80 is connected to the discharge port of the third pump 82 through a first discharge valve 81. The passage of the suction port of the third pump 82 is branched at a multi-branch part 83. The suction port of the third pump 82 is connected to a first vessel discharge valve 84 for the first culture vessel 55 and to a first vessel discharge valve 85 for the second culture vessel 57. The first vessel discharge valve 84 is connected to the second port 64 of the first culture vessel 55. In other words, in the tubing configuration, the liquid is discharged from the first vessel 62 of the first culture vessel 55 or the second culture vessel 57 to the first waste bottle 79 by the operation of the third pump 82.

On the other hand, a waste tube 87 is hermetically connected to a second waste bottle 86. The waste tube 87 is connected to the discharge port of the fourth pump 89 through a second discharge valve 88. The passage of the suction port of the fourth pump 89 is branched at a multi-branch part 90. The suction port of the fourth pump 89 is connected to a second vessel discharge valve 91 for the first culture vessel 55 and to a second vessel discharge valve 92 for the second culture vessel 57. The second vessel discharge valve 91 is connected to the fourth port 66 of the first culture vessel 55. In other words, in the tubing configuration, the liquid is discharged from the main body 59 to be the second vessel of the first culture vessel 55 or the second culture vessel 57 to the second waste bottle 86 by the operation of the fourth pump 89.

<Cell Culture Process and Observation Process>

Figure 7:
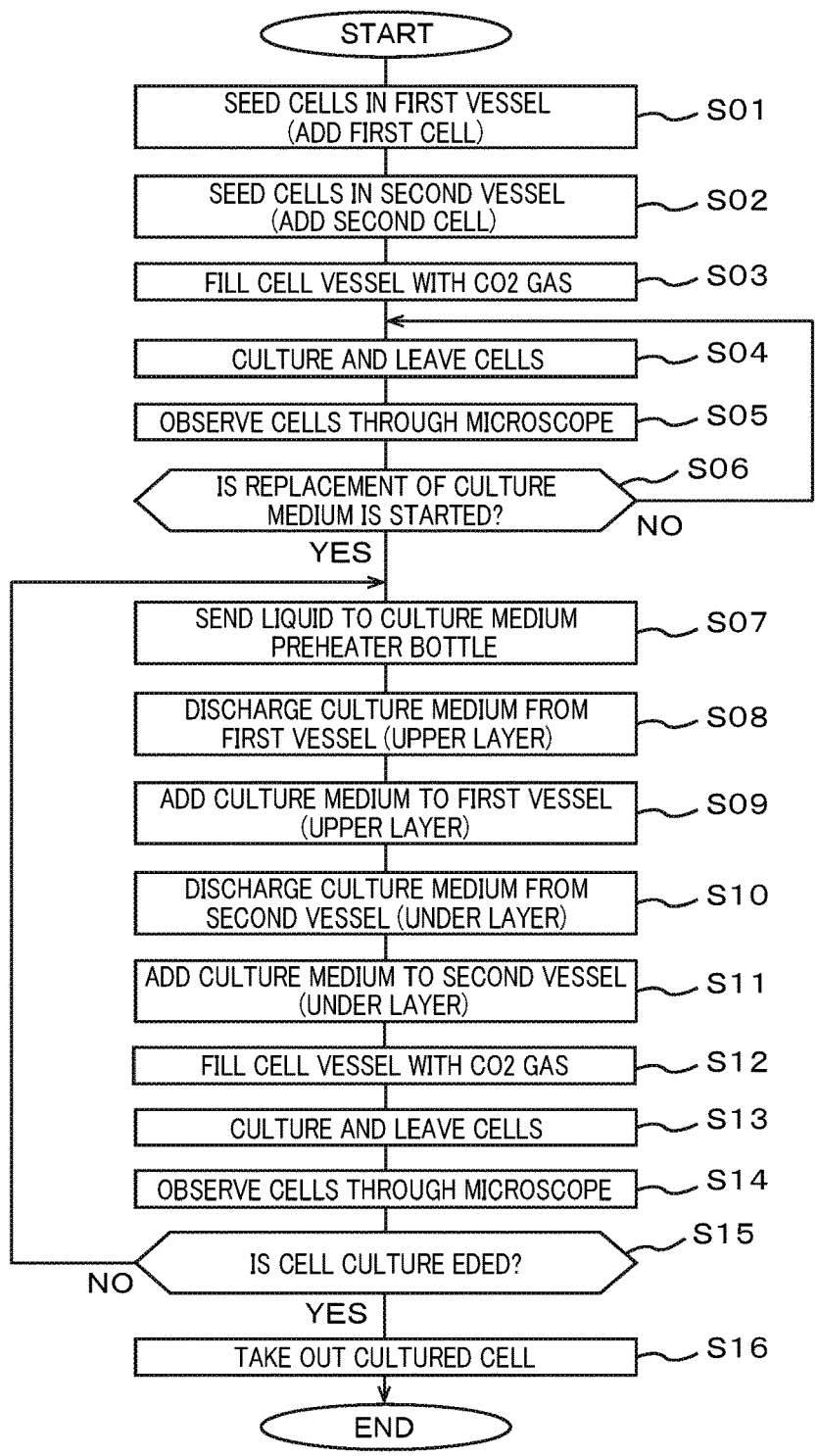
FIG. 7 is a diagram of a control flow of an automatic culture system of the automatic cell culture system according to the first embodiment.

FIG. 7 is a flowchart of the overall processes of cell culture and observation in the automatic cell culture system 31 according to the embodiment controlled by the controller 30. First, a cell is seeded in the first vessel 62 of the culture vessel (a first cell is added) (S01), and a cell is seeded in the second vessel 61 (a second cell is added) (S02). When a plurality of cell cultures is performed, the processes above are repeated. After the cell culture vessel is filled with $CO_2$ gas (S03), the cells are cultured and allowed to stand (S04), the cells are observed using a microscope, not illustrated, (S05), and it is determined whether to start to replace liquid culture media (S06).

In replacing liquid culture media, after a liquid is sent to the culture medium preheater bottle (S07), the culture medium in the first vessel is discharged (S08), a culture medium is added to the first vessel (S09), the culture medium in the second vessel is discharged (S10), a culture medium is added to the second vessel (S11), and then the cell culture vessel is filled with $CO_2$ gas (S12). When a plurality of cell cultures is performed, the processes above are repeated. Subsequently, the cells are cultured and allowed to stand (S13), the cells are observed using a microscope (S14), and then it is determined whether cell culture is ended (S15). After cell culture is ended, the cultured cells are taken out (S16).

Figure 8:
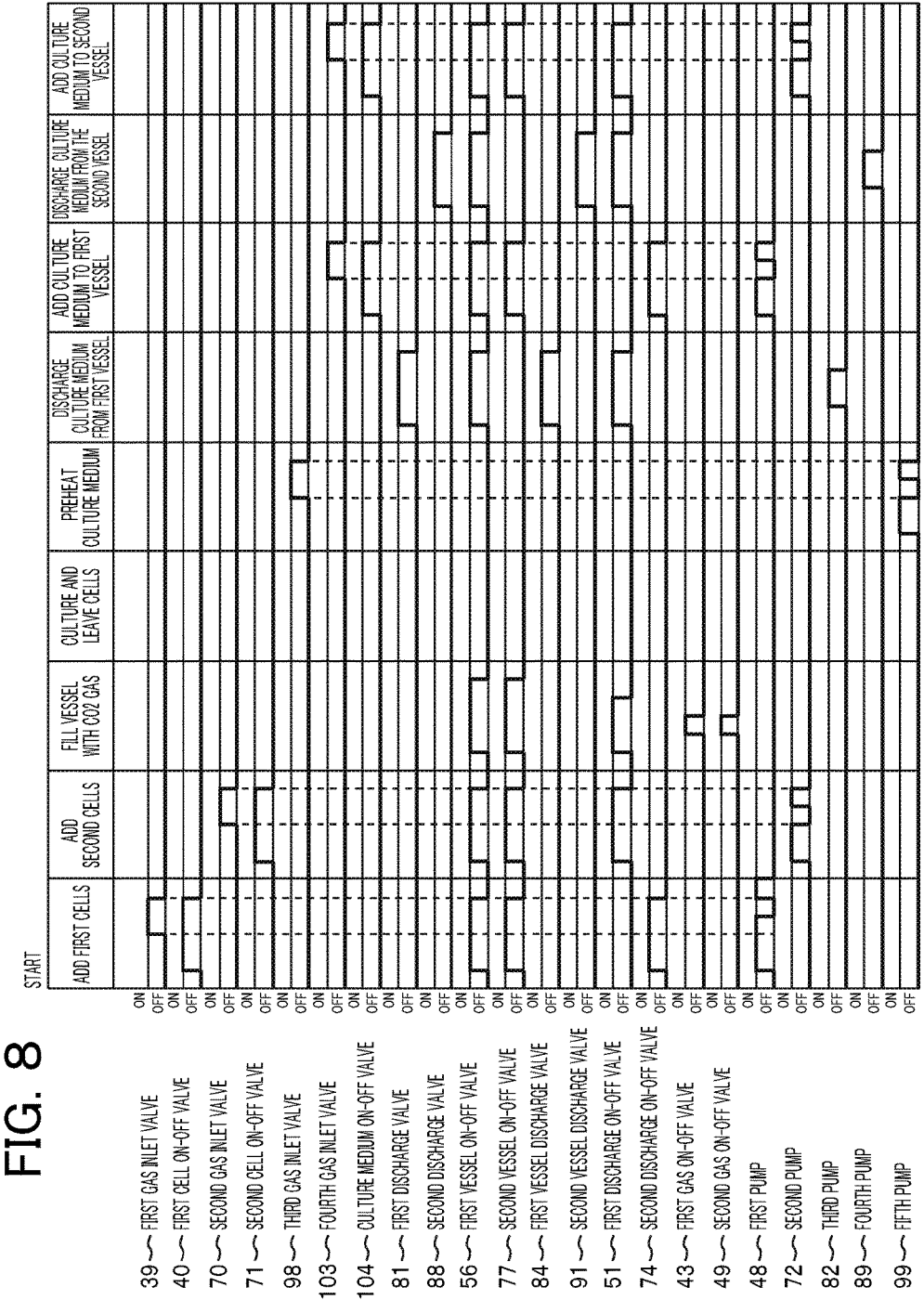
FIG. 8 is a control flowchart of the automatic cell culture system according to the first embodiment.

FIG. 8 is a time chart of liquid sending and gas supply of the first culture vessel 55 of the automatic cell culture system 31 according to the embodiment controlled by the controller 30. The horizontal axis expresses process items and a time base corresponding to Steps S01 to S04 and Steps S07 to S11 in FIG. 7. In the vertical direction, the operation timing is expressed for components in FIG. 1, i.e., 17 solenoid valves, which are the first gas inlet valve 39 to the culture medium on-off valve 104, and five roller pumps, which are the first pump 48 to the fifth pump 99. In the initial state, all the valves are off, which are closed. All the pumps are off, and liquid sending is stopped.

Cells are first seeded in the first vessel 62 in the cell culture vessel 55 (S01 in FIG. 7), and the processes follow the operation of adding the first cell. From the initial state, the first cell on-off valve 40, the first vessel on-off valve 56, the second vessel on-off valve 77, and the second discharge on-off valve 74 are turned on, and these valves are opened. The first cell on-off valve 40 then communicates with the first vessel on-off valve 56 to open the flow channel from the first cell bottle 34 to the first port 63. From the air communication filter 52 communicating with the outside air, the second discharge on-off valve 74 communicates with the second vessel on-off valve 77, and then tubes from the filter connected to the outside air to the third port 65 are opened.

Subsequently, after the first pump 48 is on for a predetermined time period, sending a cell suspension is started from the first cell bottle 34. A predetermined time period for operating the pump can be found by calculation in which a sum of a target liquid sending amount that has to be held in the first vessel and a liquid amount that is a total of the internal volumes of the tubes from the first cell bottle 34 to the branch point 38 is found in advance and then time is calculated based on the specifications of a flow rate of the pump. After an elapse of a predetermined time period, the liquid sending of the first pump 48 is stopped, and then the first gas inlet valve 39 is opened. The liquid from the branch point 38 to the first cell bottle 34 is returned to the bottle by a fall. Consequently, a quantified cell liquid suspension is prepared in the supply tube 37 in which the rear end is the branch point 38 and the tip end is the starting point of liquid sending.

Subsequently, after the first pump 48 is operated, cleaned air is sequentially supplied from the filter 41, and a cell liquid suspension is sent from the first port 63 of the cell culture vessel 55 through the first vessel on-off valve 56. In sending the suspension, the third port 65 communicates with the outside air. Thus, the pressure in the inside of the cell culture vessel 55 is adjusted to a normal pressure. In other words, in Step S01, the first port 63 and the third port 65 function as a first supply port and a first outlet port, respectively. After a predetermined amount of the suspension is injected, the first pump 48 is stopped, the opened valves are turned off, and then sending the liquid is ended. As described above, in the liquid sending unit, no liquid is held in the inside of the tubes in the termination of liquid sending. Thus, the culture medium is prevented from being dried, or from being degenerated to clog the tubes.

In the case in which a plurality of cell culture vessels is present, a cell suspension in the amount that can be allocated to the plurality of cell culture vessels is held in advance in the first cell bottle 34. In the above processes, the first vessel on-off valve 56 is closed, the first vessel on-off valve 58 in FIG. 1 is opened, the second vessel on-off valve 77 is closed, the second vessel on-off valve 78 in FIG. 1 is opened, and then the above operation is performed. Thus, a cell liquid suspension in the same amount is sent to the first vessel 62 of the cell culture vessel 57.

Subsequently, in the case in which a cell is seeded in the second vessel 61 in the cell culture vessel 55 (S02 in FIG. 7), the processes follow the operation of adding a second cell. From the initial state, the second cell on-off valve 71, the first vessel on-off valve 56, the second vessel on-off valve 77, and the first discharge on-off valve 51 are turned on, and these valves are opened. The second cell bottle 67 then communicates with the second cell on-off valve 71 and the second vessel on-off valve 77, and a flow channel to the third port 65 is opened. From the air communication filter 52 communicating with the outside air, the first discharge on-off valve 51 communicates with the first vessel on-off valve 56, and then the tubes from the filter connected to the outside air to the first port 63 are opened.

Subsequently, after the second pump 72 is on for a predetermined time period, sending the cell suspension is started from the second cell bottle 67. A predetermined time period for operating the pump can be found by calculation in which a sum of a target liquid sending amount that has to be held in the second vessel and a liquid amount that is a total of the internal volumes of the tubes from the second cell bottle 67 to the branch point 69 is found in advance and then time is calculated based on the specifications of a flow rate of the pump. After an elapse of a predetermined time period, the liquid sending of the second pump 72 is stopped, and then the second gas inlet valve 70 is opened. Thus, a quantified cell liquid suspension is prepared in the supply tube 68 in which the rear end is the branch point 69 and the tip end is the starting point of liquid sending.

Subsequently, after the second pump 72 is operated, cleaned air is sequentially supplied from the filter, and a cell liquid suspension is sent from the third port 65 of the cell culture vessel 55 through the second vessel on-off valve 77. In sending the suspension, the first port 63 communicates with the outside air. Thus, the pressure in the inside of the cell culture vessel 55 is adjusted to a normal pressure. In other words, in Step S02, the first port 63 functions as the first outlet port. On the other hand, the third port 65 functions as the first supply port. After a predetermined amount of the suspension is injected, the second pump 72 is stopped, the opened valves are turned off, and then sending the liquid is ended.

At this time, in the tubes communicating from the first port 63 to the first discharge on-off valve 51, the state is the state after the operation of adding the first cell. Thus, a slight amount of the remaining liquid culture medium is mixed with the gaseous phase in the inside of the tubes. The mixture is moved to the trap bottle 105. The liquid having passed through the inside of the liquid sending tube and reached the trap bottle 105 is condensed at the vessel side opening 107, and then dropped onto the inner bottom part of the trap bottle. The gaseous phase passes through the atmosphere side opening 108 communicating inside the bottle, reaches the air communication filter 52, and then is released to the atmosphere.

In the case in which a plurality of cell culture vessels is present, a cell suspension in the amount that can be allocated to the plurality of cell culture vessels is held in advance in the second cell bottle 67. In the above processes, the second vessel on-off valve 77 is closed, the second vessel on-off valve 78 in FIG. 1 is opened, the first vessel on-off valve 56 is closed, the second vessel on-off valve 58 in FIG. 1 is opened, and then the above operation is performed. Thus, a cell liquid suspension in the same amount is sent to the second vessel 61 of the cell culture vessel 57.

Subsequently, in the case in which the inside of the cell culture vessel 55 is filled with $CO_2$ gas (S03), the processes follow the operation of filling $CO_2$ gas. From the initial state, the first vessel on-off valve 56, the second vessel on-off valve 77, the second gas on-off valve 49, and the second discharge on-off valve 74 are turned on, and these valves are opened. The first gas on-off valve 43 then communicates with the first vessel on-off valve 56, and a flow channel to the first port 63 is opened. From the air communication filter 52, the trap bottle 105 communicates with the second discharge on-off valve 74 and the first vessel on-off valve 77, and a flow channel to the third port 65 is opened. Subsequently, after the first gas on-off valve 43 is on for a predetermined time period, $CO_2$ gas is sent from the cylinder 47 to the sparger bottle 44, and passes through the first vessel on-off valve 56 and the first port 63, and then the optimally humidified $CO_2$ gas reaches the cell culture vessel 55.

The cell culture vessel 55 is sealed, but is opened from the third port 65 to the air communication filter 52 communicating with the outside air. Thus, the pressure in the inside of the cell vessel is a pressure adjusted to the outside air pressure. The humidified $CO_2$ gas is separated into the liquid phase and the gaseous phase at the trap bottle 105. Consequently, the liquid phase is prevented from reaching the air communication filter 29, and thus the filter can be prevented from being clogged. After a predetermined amount of $CO_2$ gas is injected, first, the first gas on-off valve 43 is closed, and then the second gas on-off valve 49 is closed. When the pressure inside the culture vessel is equal to the atmospheric pressure, the other valves are closed. In the case in which a flow of the gas thus pressurized is stopped, a method is used in which the valves provided on the upstream of the gas flow are in turn closed with a time difference. This method is desirable, because the internal pressure of the cell vessel can be controlled to a value close to the value of the atmospheric pressure.

In the case in which a plurality of cell culture vessels is present, in the above processes, the second vessel on-off valve 77 is closed, the second vessel on-off valve 78 in FIG. 5 is opened, the first vessel on-off valve 56 is closed, the second vessel on-off valve 58 in FIG. 5 is opened, and then the above operation is performed. Thus, the cell culture vessel 57 is filled with $CO_2$ gas.

In cell culture, the first cell suspension is held in the first vessel 62, the second cell suspension is held in the second vessel 61, the internal space of the cell culture vessel 55 is filled with the optimally humidified $CO_2$ gas, and the temperature of the cell culture vessel 55 is kept at the optimum culture temperature. Thus, cell suspensions are allowed to stand for a predetermined time period and held, and cell culture is continued (S04). Cells in the cell suspension are attached to the upper part of the substance permeable membrane of the first vessel 62 or to the inner bottom face of the second vessel 61 for growing. Thus, the liquid culture medium with its components being changed over culture can be separated from the cells and discharged.

Cells are observed in culturing cells (S05) using a microscopic observation unit, not illustrated, in the process in which cells are cultured and allowed to stand. A phase contrast microscope is preferable for microscopic observation. An inverted optical microscope, for example, may be used. With the provision of an imaging function, the process of culturing cells under observation can be recorded, and cell culture can be more preferably preformed.

Subsequently, in the case in which the liquid culture medium is replaced from the cell culture vessel (S06), the processes follow the processes of the operation time chart in FIG. 7, i.e., the process of preheating and sending the culture medium, the process of discharging the culture medium from the first vessel, the process of adding the culture medium to the first vessel, the process of discharging the culture medium from the second vessel, and the process of adding the culture medium to the second vessel.

In the case in which the culture medium is sent for preheating (S07), in the initial state, the culture medium preheater bottle 100 communicates with the culture medium bottle through the fifth pump 99. From the lid, the culture medium preheater bottle 100 is connected to the filter communicating with the outside air. Thus, sending the culture medium is started with a pump operating time period of the fifth pump 99 corresponding to the total liquid sending amount including the target amount and the total volume of the supply tube 96 from the branch point 97 to the culture medium bottle 95. After a lapse of a predetermined time period, the third gas inlet valve 98 is opened. The liquid culture medium on the downstream of the branch point 97 is returned to the culture medium bottle 95, and the quantified liquid culture medium is prepared in the supply tube 96 in which the rear end is the branch point 97 and the tip end is the culture medium preheater bottle 100. Subsequently, after liquid sending of the fifth pump 99 is started, the liquid culture medium is sent to the inside of the culture medium preheater bottle 100. In sending the medium, the culture medium preheater bottle 100 communicates with the outside air. Thus, the pressure in the inside of the culture medium preheater bottle 100 is adjusted to a normal pressure. After a predetermined amount of the suspension is injected, the fifth pump 99 is stopped, the opened valves are turned off, and then sending the liquid is ended. For the time required to preheat the medium, in the case of a medium in a liquid amount of 50 ml at a temperature of 4° C., the temperature is increased from the temperature inside the thermostat to a low temperature for about one hour.

In the case in which a plurality of cell culture vessels is present, the liquid sending amount of the pump is adjusted in such a manner that the liquid culture medium in an amount that can be allocated to the plurality of cell culture vessels is held in advance in the culture medium preheater bottle 100. In cell culture, in the case in which a plurality of times of replacing the culture medium is scheduled, the culture medium bottle holds the liquid culture medium in an amount that can be sent to a plurality of cell culture vessels at a plurality of times, in which the amount of the liquid culture medium necessary for the plurality of cell culture vessels is multiplied by the number of times of replacing the culture medium. Thus, the culture medium can be replaced from a plurality of cell culture vessels at a plurality of times.

In the case in which the culture medium is discharged from the first vessel 62 in the cell culture vessel 55 (S08), the processes follow the operation of discharging the culture medium from the first vessel in the operation time chart in FIG. 7. From the initial state, after the first vessel on-off valve 56 and the first discharge on-off valve 51 are turned on, the first vessel discharge valve 84 and the first discharge valve 81 are turned on, these valves are opened. From the air communication filter 52 communicating with the outside air, the trap bottle 105 communicates with the first discharge on-off valve 51 and the first vessel on-off valve 56, and then the tubes from the filter connected to the outside air to the first port 63 are opened. From the first waste bottle 79, a flow channel to the second port 64 is opened through the first discharge valve 81, the third pump 82, and the first vessel discharge valve 84.

Subsequently, after the third pump 82 is on for a predetermined time period for discharging a liquid in an amount held in the first vessel 62 of the cell culture vessel 55, the liquid culture medium is sucked from the first vessel 62 to start sending the medium, and the medium reaches the first waste bottle 79. At this time, the first port 63 communicates with the outside air through the trap bottle 105. Thus, the pressure in the inside of the cell culture vessel 55 is adjusted to a normal pressure. After a predetermined amount of the medium is discharged, the third pump 82 is stopped, the opened valves are turned off, and then sending the liquid is ended.

In the case in which a plurality of cell culture vessels is present, in the above processes, the first vessel on-off valve 56 is closed, the first vessel on-off valve 58 in FIG. 5 is opened, the first vessel discharge valve 84 is closed, the first vessel discharge valve 85 in FIG. 5 is opened, and then the above operation is performed. Thus, the liquid culture medium is discharged from the first vessel 61 of the cell culture vessel 57.

In the case in which the liquid culture medium is added to the first vessel 62 (S09), the processes follow the operation of adding a culture medium to the first vessel. From the initial state, the culture medium on-off valve 104, the first vessel on-off valve 56, the second vessel on-off valve 77, and the second discharge on-off valve 74 are turned on, and these valves are opened. From the culture medium preheater bottle 100, the culture medium on-off valve 104 communicates with the first vessel on-off valve 56, and a flow channel to the first port 63 is opened. From the air communication filter 52 communicating with the outside air, the second discharge on-off valve 74 communicates with the second vessel on-off valve 77, and the tubes from the filter connected to the outside air to the third port 65 are opened. Subsequently, after the first pump 48 is on for a predetermined time period, sending the liquid culture medium from the preheater bottle 100 is started. A predetermined time period for operating the pump can be found by calculation in which a sum of a target liquid sending amount that has to be held in the first vessel and a liquid amount that is a total of the internal volumes of the tubes from the preheater bottle 100 to the branch point 102 is found in advance and then time is calculated based on the specifications of a flow rate of the pump. After an elapse of a predetermined time period, the liquid sending of the first pump 48 is stopped, and then the fourth gas inlet valve 103 is opened. Thus, the quantified liquid culture medium is prepared in the supply tube 101 in which the rear end is the branch point 102 and the tip end is the starting point of liquid sending.

Subsequently, after the first pump 48 is operated, cleaned air is sequentially supplied from the filter, and the liquid culture medium is sent from the first port 63 of the cell culture vessel 55 through the first vessel on-off valve 56. In sending the medium, the third port 65 communicates with the outside air. Thus, the pressure in the inside of the cell culture vessel 55 is adjusted to a normal pressure. In other words, in Step S09, the first port 63 and the third port 65 function as the first supply port and the first outlet port, respectively. After a predetermined amount of the suspension is injected, the first pump 48 is stopped, the opened valves are turned off, and then sending the liquid is ended.

In the case in which a plurality of cell culture vessels is present, the liquid culture medium in an amount that can be allocated to the plurality of cell culture vessels is held in advance in the culture medium preheater bottle 100. In the above processes, the first vessel on-off valve 56 is closed, the first vessel on-off valve 58 in FIG. 1 is opened, the second vessel on-off valve 77 is closed, the second vessel on-off valve 78 in FIG. 1 is opened, and then the above operation is performed. Thus, the liquid culture medium in the same amount is sent to the first vessel 62 of the cell culture vessel 57.

In the case in which the culture medium is discharged from the second vessel 61 in the cell culture vessel 55 (S10), the processes follow the operation of discharging the culture medium from the second vessel in the operation time chart in FIG. 7. From the initial state, after the first vessel on-off valve 56 and the first discharge on-off valve 51 are turned on, the second vessel discharge valve 91 and the second discharge valve 88 are turned on, these valves are opened. From the air communication filter 52 communicating with the outside air, the first discharge on-off valve 51 communicates with the first vessel on-off valve 56, and then the tubes from the filter connected to the outside air to the first port 63 are opened. From the second waste bottle 86, a flow channel to the third port 66 is opened through the second discharge valve 88, the fourth pump 89, and the second vessel discharge valve 91.

Subsequently, after the fourth pump 89 is on for a predetermined time period for discharging a liquid in an amount held in the second vessel 61 of the cell culture vessel 55, the liquid culture medium is sucked from the second vessel 61 to start sending the medium, and the medium reaches the second waste bottle 86. In sending the medium, the first port 63 communicates with the outside air. Thus, the pressure in the inside of the cell culture vessel 55 is adjusted to a normal pressure. After a predetermined amount of the medium is discharged, the fourth pump 89 is stopped, the opened valves are turned off, and then sending the liquid is ended.

In the case in which a plurality of cell culture vessels is present, in the above processes, the first vessel on-off valve 56 is closed, the first vessel on-off valve 58 in FIG. 1 is opened, the second vessel discharge valve 91 is closed, the second vessel discharge valve 92 in FIG. 1 is opened, and then the above operation is performed. Thus, the liquid culture medium is discharged from the second vessel 61 of the cell culture vessel 57.

In the case in which the liquid culture medium is added to the second vessel 61 (S11), the processes follow the operation of adding a culture medium to the second vessel. From the initial state, the culture medium on-off valve 104, the first vessel on-off valve 56, the second vessel on-off valve 77, and the first discharge on-off valve 51 are turned on, and these valves are opened. From the culture medium preheater bottle 100, the culture medium on-off valve 104 communicates with the second vessel on-off valve 77, and then a flow channel to the third port 65 is opened. From the air communication filter 52 communicating with the outside air, the first discharge on-off valve 51 communicates with the first vessel on-off valve 56, and then the tubes from the filter connected to the outside air to the first port 63 are opened.

Subsequently, after the second pump 72 is on for a predetermined time period, sending the liquid culture medium from the preheater bottle 100 is started. A predetermined time period for operating the pump can be found by calculation in which a sum of a target liquid sending amount that has to be held in the second vessel and a liquid amount that is a total of the internal volumes of the tubes from the preheater bottle 100 to the branch point 102 is found in advance and then time is calculated based on the specifications of a flow rate of the pump. After an elapse of a predetermined time period, the liquid sending of the second pump 72 is stopped, and then the fourth gas inlet valve 103 is opened. Thus, the quantified liquid culture medium is prepared in the supply tube 102 in which the rear end is the branch point 102 and the tip end is the starting point of liquid sending. Subsequently, after the second pump 72 is operated, cleaned air is sequentially supplied from the filter, and the liquid culture medium is sent from the third port 65 of the cell culture vessel 55 through the second vessel on-off valve 77. At this time, the first port 63 communicates with the outside air. Thus, the pressure in the inside of the cell culture vessel 55 is adjusted to a normal pressure. In other words, in Step S11, the first port 63 functions as the first outlet port. On the other hand, the third port 65 functions as the first supply port. After a predetermined amount of the suspension is injected, the second pump 72 is stopped, the opened valves are turned off, and then sending the liquid is ended.

In the case in which a plurality of cell culture vessels is present, the liquid culture medium in an amount that can be allocated to the plurality of cell culture vessels is held in advance in the culture medium preheater bottle 100. In the above processes, the second vessel on-off valve 77 is closed, the second vessel on-off valve 78 in FIG. 1 is opened, the first vessel on-off valve 56 is closed, the first vessel on-off valve 58 in FIG. 1 is opened, and then the above operation is performed. Thus, the liquid culture medium in the same amount is sent to the second vessel 62 of the cell culture vessel 57. Subsequently, the cell culture vessel 55 is filled with the atmosphere. Thus, in order to fill the cell culture vessel 55 with $CO_2$ gas, the filing process of $CO_2$ gas (S12) is similarly performed as described above.

In the case in which a plurality of cell culture vessels is present, in the above processes, the first vessel on-off valve 56 is closed, the first vessel on-off valve 58 in FIG. 1 is opened, the second vessel on-off valve 77 is closed, the second vessel on-off valve 78 in FIG. 1 is opened, and then the above operation is performed. Thus, the cell culture vessel 57 is filled with $CO_2$ gas.

In the following, a specific example of a method for preparing corneal epithelial tissue using the culture of corneal epithelial cells using the automatic cell culture system according to the first embodiment and a result based on the method will be described.

<Configurations of the Automatic Cell Culture System and the Liquid Sending Device>

In the cell culture vessels illustrated in FIG. 1, the main body 59, the lid 60, and the first port 63 to the fourth port 66 were prepared by injection molding with polycarbonate for their materials. For the first vessel, a cell culture insert (six wells), model No. 353090, made by Becton, Dickinson and Company, was used. The substance permeable membrane 9 was polymerized with N-isopropylacrylamide, which is a temperature responsive polymer monomer, by electron beams. Thus, a temperature responsive culture surface was prepared. For the second vessel, a 35-mm cell culture surface processed dish, model No. 430165, made by Corning Incorporated, was used.

For the thermostat, an incubator (Toyo Engineering Works, Ltd., model No. TVHA60WA12A) was used. The chamber temperature of the thermostat was operated at a temperature of 37° C. For the refrigerator unit, an electronic low temperature chamber (Toyo Engineering Works, Ltd., model No. THS030PA) was used. The chamber temperature of the refrigerator unit was operated at a temperature of 4° C.

For the solenoid valve, a pinch valve (the fluid pressure is 0.15 MPa, made by Takasago Electric, Inc., model No. PSK-1615NC-9) was used. For a supply tube corresponding to this solenoid valve, a silicone rubber tube (the inner diameter is ⅟16 inch, and the outer diameter is ⅛ inch, made by Saint-Gobain Crystals, model No. 3350) was used. The pumps were used in combination of a tube pump (the discharge/suction pressure is +/−0.1 MPa, Welco Co., Ltd., model No. DSW2-S1AA-WP) and a silicone rubber tube for a drawing tube (the inner diameter is ¹⁄₁₆ inch, and the outer diameter is ⅛ inch, made by Saint-Gobain Crystals, model No. 3355L). This tube pump has a roller that is detachable from the motor of the main body. Thus, the sterilization processes can be performed with a silicone rubber tube in a length of 13 cm being wound around the roller. The flow rate of the pump was 0.15 ml/sec. at an input of DC 12 V, by actual measurement.

For the cell bottle and the culture medium preheater bottle, a closed system centrifuge tube (the capacity is 50 ml, Corning Incorporated, model No. 11705) was used. This tube includes a vessel, a lid, a tube for adjusting the atmospheric pressure provided on the lid, and a filter, which are in advance sterilized. For the culture medium bottle, a closed system Erlenmeyer flask (the capacity is 1 L, Corning Incorporated, model No. 11440) was adopted. This flask includes a supply tube (the inner diameter is ⅛ inch), a vessel, a lid, a tube for adjusting the atmospheric pressure provided on the lid, and a filter, which are in advance sterilized.

For the waste bottle, Flexboy Bag (the capacity is one liter, Sartorius AG, model No. FFB103547) was used. For the sparger bottle, a gas washing bottle (the capacity is 500 ml, AS ONE Corporation, model No. 6-129-02) was used. For the gas exchange unit, a filter (the filter size is 15×15 mm, AS ONE Corporation, model No. 2-554-10) was used. The bottle and the filter were used in combination.

For the filters for the gas inlet valve or the sparger bottle communicating with the outside air, Midisart 2000 (the mesh size is 0.22 μm, Sartorius AG, model No. 17805-E) was used.

For tubes used for the components other than the solenoid valve and the pump, Tygon S-50-HL made of vinyl chloride (the inner diameter is ¹⁄₁₆ inch, and the outer diameter is ⅛ inch, made by Saint-Gobain Crystals, model No. 63010-390) was used. For the branching and joining tubes, SMC coupling series (Colder Products Company) was used. In detail, for joining two branches, Y Fitting (the joint diameter is ¹⁄₁₆ inch, model No. HY291) was used. For linear coupling, Straight Fitting (the joint diameter is ¹⁄₁₆ inch, model No. HS291) was used.

The configuration of the liquid sending device according to the embodiment will be described based on the process of sending the cell suspension to the vessel 1 of the cell culture vessel. The first cell bottle 34 is provided with a supply tube in a length of 10 cm (the inner diameter is 3.7 mm). Between the supply tube and the branch point 38, a silicone rubber tube in a length of 20 cm is provided (the inner diameter is ¹⁄₁₆ inch, i.e., 1.58 mm). In the following, the specifications are the same. The branch point 38 was connected to the suction port of the first pump 48 using a silicone rubber tube in a length of 15 cm. For the drawing tube in the first pump 48, a silicone rubber tube in a length of 13 cm was connected. The discharge port of the first pump 48 was connected to the multi-branch part 54 using a Tygon S-50-HL tube in a length of 80 cm. The multi-branch part 54 was connected to the first port 63 using a Tygon S-50-HL tube in a length of 1.5 m. For the trap bottle, a reinforced bottle made of transparent polycarbonate (the capacitance/capacity is 250 ml, Nalgene Nunc International Corporation) and a screw cap with a connector were used in combination.

The above liquid sending amount of a cell suspension of 1.5 ml was determined as follows. The internal volume of the tubes from the supply tube to the branch point 38 is the maximum liquid amount that returns to the liquid bottle when a gas is introduced. As a result by actual measurement, the volume was 1.088 ml. A pump operating time period found from the total amount of the returning amount and the liquid sending amount was 17.3 seconds. For a time period for sending a liquid to the vessel after a gas was introduced, a time period of 60 seconds was further given, and the liquid sending amount was actually measured. The liquid sending amount was 1.48 ml±0.08 ml (deviation in which measurement was repeated for 10 times). On the plurality of cell culture vessels, experiments were conducted in which the suspension was alternately sent to the vessel 1 and the vessel 2. Reproducibility was equivalent in both of the vessels. Using the automatic cell culture system and the trap bottle according to the embodiment, a liquid culture medium that has not reached the vessel remains in the liquid sending tube through which a liquid culture medium has been sent. The gaseous phase then moves to send the liquid culture medium inside the liquid sending tube, and the liquid culture medium passes through the trap bottle. At this time, the liquid culture medium is separated into the liquid phase and the gaseous phase in the trap bottle. Thus, the liquid phase is prevented from reaching the air communication filter, which prevents the filter from being clogged. Consequently, the internal pressures of the culture vessels can be maintained at a normal pressure.

In the configuration of the trap bottle as the collecting unit for collecting liquids, such as moisture, in order to improve the efficiency of separating the gaseous phase from the liquid phase, the trap bottle itself is held in the refrigerator, as described above. Thus, the temperature of a gas is dropped as passing through the bottle, which allows the promotion of condensation reactions to speed up liquefaction. An adsorbent 109, such as synthetic zeolite, is held in the inside of the trap bottle, which allows the promotion of adsorbing moisture and the use of moisture.

Corneal epithelial cells were formed in a cell suspension. The suspension was held in the first cell bottle 34. NIH-3T3 cells were suspended in a culture medium in the size of 2×104/cm$^2$, and then held in the second cell bottle 67. For a culture medium for replacement, a KCM culture medium in an amount of 500 ml was held in the culture medium bottle 95, and disposed in the refrigerator 33.

The inside of the automatic cell culture system 31 was held constantly at a temperature of 37° C. Ten cell culture vessels were disposed. Automatic culture processes were started. The liquid sending amount to the upper layer is 1.5 ml. The liquid sending amount to the under layer is 2.0 ml. The liquid sending amount of the culture medium is the same. In discharging a liquid, in order to discharge all the amounts, the pumps were operated for a pump operating time period corresponding to an amount of 3 ml for a discharge amount from the upper layer. The pumps were operated for a pump operating time period corresponding to an amount of 4 ml for a discharge amount from the under layer. $CO_2$ gas was controlled to a humidity of 95% H. The supply amount of $CO_2$ gas was a flow rate of 0.1 L/min. $CO_2$ gas was excessively supplied over an internal volume of 20 cm$^3$ in the cell culture vessel. A solenoid valve opening time period was set to one minute (100 ml). The operation time chart described above was in conformance with the processes in FIG. 7.

After culture was started, the culture medium was replaced once on day 5, day 7, day 9, day 10, day 11, day 12, day 13, day 14, day 15, and day 16. $CO_2$ gas was supplied for six times a day for every four hours. Microscopic observation was conducted from day 5 once everyday. Ten areas of the first cell and ten areas of the second cell were taken from each of the cell culture vessels for data for determining the growing state of cells.

On day 16 of the culture, after the culture medium was replaced, cell culture was ended. Ten cell culture vessels were taken out. The cell culture vessels were placed in a safety cabinet, and allowed to stand at an ambient temperature (about 25° C.) for 30 minutes. In accordance with the description above, the first vessel was taken out. After that, for a substrate film, a hydrophilic PVDF membrane cut in a doughnut shape (made by Merck Millipore Corporation) was used. Sheet-like cells were removed and recovered from the surface of the substance permeable membrane. As a result, corneal epithelial tissue prepared in the automatic cell culture system according to the embodiment had the same size and thickness equivalent in ten sheet-like cells, which were successfully stably removed and recovered. In the comparison in the growing process with microscopic images, no significant differences were observed.

Second Embodiment

A second embodiment will be described. The second embodiment is a configuration in which the trap bottle of the automatic cell culture system according to the first embodiment described in detail is used as a liquid bottle for temporarily storing an excess liquid produced in the process of culturing, or for temporarily storing a liquid introduced for cleaning tubes.

For example, in FIG. 1, in the process of the culture medium replacement, the liquid sending amount sent from the culture medium bottle 95 is adjusted in such a manner that the culture medium preheater bottle 100 holds a liquid culture medium for one replacement. Typically, the required amount of a liquid culture medium for one replacement is constant for one culture period. However, in order to cope with the fluctuations in the liquid sending amount, a greater amount of movement is held in the culture medium preheater bottle 100. The following is a problem here. After the process for one culture medium replacement is ended, the culture medium preheater bottle 100 holds an unused liquid culture medium. In the subsequent culture medium replacement, the culture medium preheater bottle 100 is to have a mixture of two liquid culture media with different temperature history in sending a liquid culture medium from the culture medium bottle 95. The following is another problem. When the culture medium replacement process proceeds in this manner, liquid culture media with different temperature history are used in every culture medium replacement. Thus, the reproducibility of the cell culture processes is uncertain.

In typical manual cell culture, a culture medium is separated into a small amount and then preheated. A culture medium unused in culture medium replacement is discarded. A new dispensing bottle is again prepared for the subsequent culture medium replacement. In the second embodiment, in conformance with typical cell culture processes, an excess liquid culture medium, which has not been used, is moved to empty out the culture medium preheater bottle. Thus, the cell culture processes can be reliably reproduced in every culture medium replacement. More specifically, the liquid culture medium does not pass through the cell culture vessel. The liquid culture medium is temporarily stored in the trap bottle using the liquid sending pump. Thus, the culture medium preheater bottle can be emptied.

Figure 9:
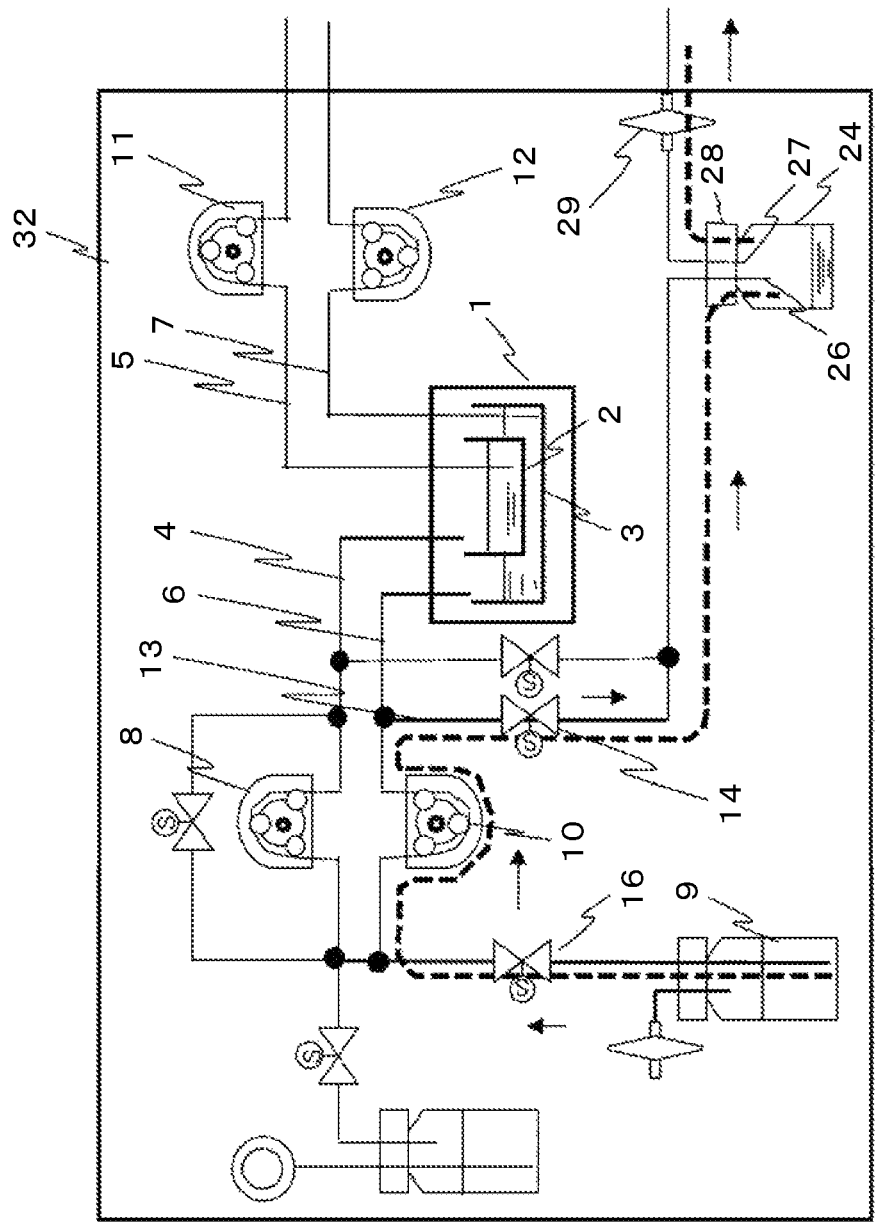
FIG. 9 is an illustration of an automatic cell culture system according to a second embodiment in the state in which a liquid is moved and stored.

FIG. 9 is a diagram in the case in which a liquid culture medium is directly sent from the liquid bottle 9 to the trap bottle 24 and temporarily stored on the trap bottle 24. In FIG. 9, the device configuration in the second embodiment is the same as the device configuration of the automatic cell culture system according to the first embodiment illustrated in FIGS. 5 and 6. After the discharge on-off valve 14 is opened, the other valves are closed, and then the second pump 10 is operated, a liquid starts to move from the liquid bottle 9 along the orientation of broken lines and arrows. On the upstream side from the liquid sending tube 6, the tube is connected to the culture vessel 1 through the liquid sending tube 4 of the culture vessel 1. When the first pump 8, the third pump 11, and the fourth pump 12 for discharge are not operated, the culture vessel 1 is closed like a valve, and the discharge side is hermetically kept. Thus, the liquid from the liquid bottle 9 does not pass through the culture vessel. The liquid passes through the discharge tube 13 and the discharge on-off valve 14, and reaches the trap bottle 24. After the second pump 10 is operated for a time period that corresponds to a time period to empty out the liquid bottle 9, all the valves are closed.

In the configuration of the automatic culture system 31 in FIG. 1, the liquid medium can be directly sent from the culture medium preheater bottle 100, which is a liquid bottle, and temporarily stored in the trap bottle 105. After the culture medium on-off valve 104 and the first discharge on-off valve 51 are opened, the other valves are closed, and then the first pump 48 is operated, the remaining liquid culture medium starts to move from the culture medium preheater bottle 100. On the upstream side of the liquid sending tube 50, the first vessel on-off valve 56 and the first vessel on-off valve 58 are closed. Thus, the liquid culture medium does not pass through the culture vessel, but passes through the vessel side opening 107 and the first discharge on-off valve 51, and then reaches the trap bottle 105 corresponding to the trap bottle 24. After the first pump 48 is operated for time corresponding to time to empty out the culture medium preheater bottle 100, all the valves are closed.

In the operation time chart of automatic cell culture in FIG. 7, the process of moving an excess liquid culture medium is desirably performed after the process of culture medium replacement (from Steps S08 to S11) is completed. The following is the reason. In the $CO_2$ gas exchange work later, the gas is sent to move the liquid culture medium remaining in the discharge tube 13, which exerts the effect that can keep the inside of the discharge tube clean.

As described above in detail, in accordance with the automatic cell culture system according to the present invention, a liquid culture medium that has not reached the vessel remains in the liquid sending tube through which a liquid culture medium has been sent. The gaseous phase then moves to causes the liquid culture medium to move in the liquid sending tube, and the liquid culture medium passes through the trap bottle. At this time, the liquid phase is separated from the gaseous phase in the trap bottle. Thus, the liquid phase is prevented from reaching the air communication filter, and the filter is prevented from being clogged. Consequently, the internal pressure of the culture vessel can be maintained at a normal pressure.

Water vapor contained in a gas communicating in the liquid sending tube is separated into the liquid phase and the gaseous phase while passing through the trap bottle. Thus, water vapor is prevented from reaching the air communication filter, and the filter is prevented from being clogged. Consequently, the internal pressure of the culture vessel can be maintained at a normal pressure.

Holding the trap bottle at a temperature lower than a room temperature improves the efficiency of condensing a liquid from the gaseous phase containing the liquid. Thus, the liquid phase is prevented from reaching the air communication filter, and the filter is prevented from being clogged.

Consequently, the internal pressure of the culture vessel can be maintained at a normal pressure.

The trap bottle of the automatic cell culture system according to the present invention can be used for temporarily storing a liquid its inside, contributing to achieving the continuous operation of the system for a long time.

The present invention is not limited to the foregoing embodiments. The present invention includes various modifications. For example, the foregoing embodiments are described in detail for better understanding the present invention. The present invention is not necessarily limited to ones including all the configurations having been described. A part of the configuration of the embodiments can be added, removed, or replaced with the other configurations. For example, in order to improve the separation efficiency of the liquid phase from the gaseous phase, passages to the trap bottle, which is the collecting unit that collects liquids, such as moisture, can be cooled with a cooling pipe, for example.

LIST OF REFERENCE SIGNS 1, 55, 57 Culture vessel
2, 62 First vessel
3, 61 Second vessel
4, 6, 50, 73 Liquid sending tube
5, 7 Discharge tube
8, 48 First pump
9 Liquid bottle
10, 72 Second pump
11, 82 Third pump
12, 89, Fourth pump
13, 51, 74 Discharge tube
14 Discharge on-off valve
15, 29, 52 Air communication filter
16 Liquid on-off valve
17, 47 Gas cylinder
18 Pure water
19, 44 Sparger bottle
20, 43 First gas on-off valve
21 Gas tube
22, 49 Second gas on-off valve
24, 105 Trap bottle
26, 107 vessel side opening
27, 108 Atmosphere side opening
28, 106 Lid
30 Controller
31 Automatic cell culture system
32 Thermostat
33 Refrigerator
34, 67 Cell bottle
35 Atmospheric pressure adjusting tube
36, 45 Filter
37, 68, 96, 101 Supply tube
38, 69, 97, 102 Branch point
39, 70, 98, 103 Gas inlet valve
40, 71 Cell on-off valve
42 Common tube
46 Pressure control valve
54, 76, 83, 90 Multi-branch part
56, 58 First vessel on-off valve
59 Main body
60 Lid
63 First port
64 Second port
65 Third port
66 Fourth port
77, 78 Second vessel on-off valve
79, 86 Waste bottle
80, 87 Waste tube
81 First discharge valve
84, 85 First vessel discharge valve
88 Second discharge valve
91, 92 Second vessel discharge valve
95 Culture medium bottle
99 Fifth pump
100 Culture medium preheater bottle
104 Culture medium on-off valve

The invention claimed is:

1. An automatic cell culture system comprising:
a culture vessel comprising a first vessel and a second vessel, the first vessel being positioned within the second vessel and having a culture surface formed of a permeable membrane;
wherein the first vessel comprises a first port configured to supply a liquid into the first vessel and discharge a gas from the first vessel, and a second port configured to discharge a liquid from the first vessel;
wherein the second vessel comprises a third port configured to supply a liquid into the second vessel and discharge a gas from the second vessel, and a fourth port configured to discharge a liquid from the second vessel;
the culture vessel further comprising:
at least one flow channel for discharging the gas discharged from the first port and the third port to outside air at atmospheric pressure;
at least one filter provided in the at least one flow channel; and
at least one collecting unit disposed between the first port and the third port, and the at least one filter in the at least one flow channel, the at least one collecting unit collecting moisture from the discharged gas.

2. The automatic cell culture system according to claim 1, wherein the at least one collecting unit comprises a trap bottle.

3. The automatic cell culture system according to claim 2, further comprising a refrigerator unit that holds the trap bottle at a low temperature.

4. The automatic cell culture system according to claim 2, wherein the trap bottle is used once.

5. The automatic cell culture system according to claim 2, wherein the trap bottle is transparent.

6. The automatic cell culture system according to claim 2, wherein the trap bottle comprises a lid, through which an atmosphere side opening and a culture vessel side opening are penetrated and
an opening end of the atmosphere side opening is positioned higher than an opening end of the culture vessel side opening.

7. The automatic cell culture system according to claim 2, further comprising a liquid bottle configured to hold the liquid supplied to the first supply port,
wherein the trap bottle stores the liquid supplied from the liquid bottle, not via the culture vessel.

8. The automatic cell culture system according to claim 1, wherein the at least one collecting unit comprises a trap bottle.

9. The automatic cell culture system according to claim 8, wherein the trap bottle holds an adsorbent in an inside thereof.

10. The automatic cell culture system according to claim 8, further comprising a refrigerator unit configured to hold the trap bottle at a low temperature.

11. The automatic cell culture system according to claim 8, wherein the trap bottle is used once.

12. The automatic cell culture system according to claim 8, wherein the trap bottle is transparent.

13. The automatic cell culture system according to claim 8,
wherein the trap bottle comprises a lid through which an atmosphere side opening and a culture vessel side opening are penetrated and
an opening end of the atmosphere side opening is positioned higher than an opening end of the culture vessel side opening.

14. The automatic cell culture system according to claim 8,
further comprising a liquid bottle configured to hold the liquid supplied to the first supply port,
wherein the trap bottle stores the liquid supplied from the liquid bottle, not via the culture vessel.

\* \* \* \* \*